United States Patent
Dufresne et al.

(10) Patent No.: US 8,548,174 B2
(45) Date of Patent: Oct. 1, 2013

(54) MODULAR ELECTRONIC BIOSENSOR WITH INTERFACE FOR RECEIVING DISPARATE MODULES

(75) Inventors: Joel R. Dufresne, St. Paul, MN (US); Hatim M. Carim, West St. Paul, MN (US); Thomas E. Drummond, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 881 days.

(21) Appl. No.: 12/531,882

(22) PCT Filed: Mar. 20, 2008

(86) PCT No.: PCT/US2008/057680
§ 371 (c)(1),
(2), (4) Date: Sep. 18, 2009

(87) PCT Pub. No.: WO2008/118750
PCT Pub. Date: Oct. 2, 2008

(65) Prior Publication Data
US 2010/0056956 A1  Mar. 4, 2010

Related U.S. Application Data

(60) Provisional application No. 60/919,574, filed on Mar. 23, 2007, provisional application No. 60/919,742, filed on Mar. 23, 2007.

(51) Int. Cl.
*A61B 7/04* (2006.01)
*A61B 7/00* (2006.01)

(52) U.S. Cl.
USPC .............................................. 381/67; 600/586

(58) Field of Classification Search
USPC ........................ 381/67, 71.2; 600/586, 528
See application file for complete search history.

(56) References Cited

U.S. PATENT DOCUMENTS

| | | | |
|---|---|---|---|
| 3,862,379 | A | 1/1975 | Pless |
| 3,906,160 | A | 9/1975 | Nakamura et al. |

(Continued)

FOREIGN PATENT DOCUMENTS

| | | |
|---|---|---|
| DE | 10164758 | 5/2004 |
| WO | WO 01/78604 | 10/2001 |
| WO | WO 2004/002191 | 12/2003 |

OTHER PUBLICATIONS

Houtsma et al., "A Noise-Immune Stethoscope for Use in Noisy Environments," 4th ASA/ASJ Joint Meeting, Honolulu, HI, Dec. 2, 2006, pp. 1-6; retrieved from the Internet on Aug. 14, 2008 <URL: http://www.acoustics.org/press/152nd/houtsma.html>.

(Continued)

*Primary Examiner* — Fan Tsang
*Assistant Examiner* — Eugene Zhao
(74) *Attorney, Agent, or Firm* — Ann K. Gallagher

(57) ABSTRACT

A modular electronic biosensor includes a housing configured for hand-held manipulation and a base module comprising a module interface configured to receive one of a multiplicity of disparate detachable modules, such as a transducer module and an output module. A transducer of the transducer module is configured to sense a property of the human body and the output module is configured to output a signal comprising transducer signal information. The module interface includes a module connector for receiving a connector of the detachable module to facilitate signal transmission therebetween, a mechanical retention mechanism configured to retentively engage the detachable module, and a sealing arrangement disposed to provide sealing between the base module and the detachable module when attached to the base module. A processor is coupled to the module connector and configured to communicatively couple with each of the detachable and interchangeable modules when attached to the base module.

28 Claims, 18 Drawing Sheets

(56) References Cited

U.S. PATENT DOCUMENTS

| | | | |
|---|---|---|---|
| 4,254,302 A | 3/1981 | Walshe | |
| 4,534,058 A | 8/1985 | Hower | |
| 4,618,986 A | 10/1986 | Hower | |
| 4,723,555 A | 2/1988 | Shue | |
| 4,878,501 A | 11/1989 | Shue | |
| 5,027,825 A | 7/1991 | Phelps et al. | |
| 5,295,485 A * | 3/1994 | Shinomura et al. | 600/443 |
| 5,467,775 A | 11/1995 | Callahan et al. | |
| 5,701,904 A | 12/1997 | Simmons et al. | |
| 5,708,725 A | 1/1998 | Ito | |
| 5,812,678 A | 9/1998 | Scalise et al. | |
| 5,960,089 A | 9/1999 | Bouricius et al. | |
| 6,005,951 A | 12/1999 | Grasfield et al. | |
| 6,028,942 A | 2/2000 | Greenberger | |
| 6,083,156 A | 7/2000 | Lisiecki | |
| 6,533,736 B1 | 3/2003 | Moore | |
| 7,024,001 B1 | 4/2006 | Nakada | |
| 7,091,879 B2 | 8/2006 | Swetlik | |
| 7,998,091 B2 * | 8/2011 | Carim et al. | 600/586 |
| 2002/0055684 A1 | 5/2002 | Patterson | |
| 2003/0002685 A1 | 1/2003 | Werblud | |
| 2003/0139671 A1 * | 7/2003 | Walston et al. | 600/437 |
| 2004/0116969 A1 | 6/2004 | Owen et al. | |
| 2004/0228494 A1 | 11/2004 | Smith | |
| 2005/0119584 A1 | 6/2005 | Carter | |
| 2005/0232434 A1 | 10/2005 | Andersen | |
| 2007/0106179 A1 | 5/2007 | Bagha et al. | |
| 2007/0113649 A1 | 5/2007 | Bharti et al. | |
| 2007/0113654 A1 | 5/2007 | Carim et al. | |
| 2008/0013747 A1 * | 1/2008 | Tran | 381/67 |
| 2009/0279708 A1 * | 11/2009 | Habboushe | 381/67 |

OTHER PUBLICATIONS

VIASYS Healthcare Inc., "Nicolet StethoDop™ Vascular Doppler," 2 pages, 2004.

* cited by examiner

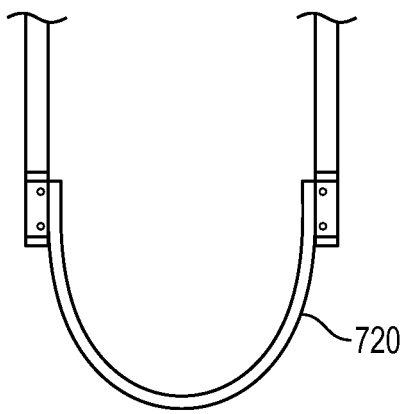
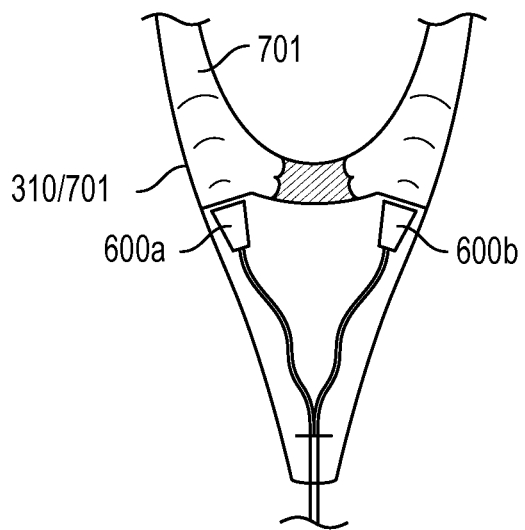
*Fig. 11B*  *Fig. 11C*
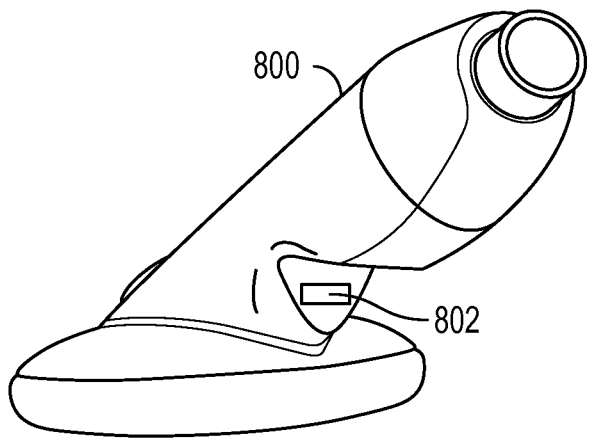
*Fig. 12A*
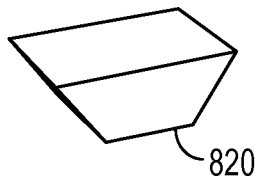 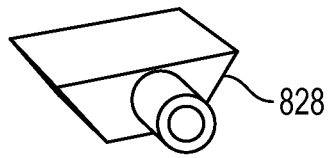
*Fig. 12B*  *Fig. 12C*

MODULAR ELECTRONIC BIOSENSOR WITH INTERFACE FOR RECEIVING DISPARATE MODULES

CROSS REFERENCE TO RELATED APPLICATIONS

This is a US National Stage filing under 35 U.S.C. §371 of PCT Application No. PCT/US2008/057680, filed Mar. 20, 2008, which claims priority to U.S. Provisional Application No. 60/919,742, filed Mar. 23, 2007 and U.S. Provisional Application No. 60/919,574, filed Mar. 23, 2007, the disclosures of which are each incorporated herein by reference in their entirety.

FIELD OF THE INVENTION

The present invention relates to medical sensing devices and, more particularly, to biosensors and systems incorporating biosensors that employ one or more detachable modules of varying configuration and functionality.

BACKGROUND

A variety of devices have been developed to detect sounds produced by the body, such as heart sounds and lung sounds. Known devices range from primarily mechanical devices, such as the stethoscope, to various electronic devices, such as microphones and transducers. The stethoscope, for example, is a fundamental tool used in the diagnosis of diseases and conditions of the cardiovascular system. It serves as the most commonly employed technique for diagnosis of such diseases and conditions in primary health care and in circumstances where sophisticated medical equipment is not available, such as remote areas.

Clinicians readily appreciate that detecting relevant cardiac symptoms and forming a diagnosis based on sounds heard through a stethoscope, for example, is a skill that can take years to acquire and refine. The task of acoustically detecting abnormal cardiac activity is complicated by the fact that heart sounds are often separated from one another by very short periods of time, and that signals characterizing cardiac disorders are often less audible than normal heart sounds.

SUMMARY OF THE INVENTION

The present invention is generally directed to a modular approach to configuring an electronic medical system or biosensor, such as an electronic stethoscope or other electronic medical diagnostic device. Embodiments of the present invention are directed to electronic biosensors comprising a housing configured for hand-held manipulation by a clinician. The biosensor includes a transducer supported by the housing and configured to sense a property of the human body, such as a manifestation of acoustic energy produced by matter of biological origin. The transducer of the biosensor may be configured to sense other properties of the human body, such as flow or volume of a fluid (e.g., a body fluid or air during inspiration/expiration), a biopotential (e.g., action potentials, such as cardiac, nervous system, muscle, and glandular action potentials), and a structural or compositional property of the human body (e.g., property of bone (density), soft tissue, organs, blood, blood gasses and blood chemistry).

In accordance with some embodiments, a modular electronic biosensor includes a housing configured for hand-held manipulation relative to a person's body surface and comprising a base module. The base module includes a multiplicity of module interfaces configured to engage a multiplicity of detachable modules. The detachable modules are preferably of disparate type or provide disparate functionality. For example, the multiplicity of detachable modules includes at least one of a detachable transducer module and a detachable output module. The transducer module comprises a transducer configured to sense a property of the person's body and the output module is configured to output a signal that includes transducer signal information.

Each of the module interfaces of the base module comprises one or more of a module connector, a mechanical retention mechanism, and a sealing arrangement. A preferred module interface typically includes each of a connector, a mechanical retention mechanism, and a sealing arrangement, although not all of these features are required for all biosensor embodiments.

According to some embodiments, each of the multiplicity of module interfaces of the base module comprises a module connector configured to receive a connector of a detachable module and to facilitate signal transmission between the respective connectors. Each module interface may further include a mechanical retention mechanism configured to detachably and retentively engage a mechanical engagement arrangement of the detachable module. Each module interface may also include a sealing arrangement disposed to provide sealing between the base module and the detachable module when the detachable module is attached to the base module. Some or all of these module interface features may be provided on the biosensor depending on the particular biosensor configuration.

The modular electronic biosensor includes a processor coupled to each of the module connectors and configured to communicatively couple with each of the detachable modules when the detachable modules are attached to the base module. The housing provides for preserving ergonomic efficiency for facilitating hand-held manipulation relative to the person's body surface after attachment of the detachable modules to the base module. Preserving ergonomic efficiency of a biosensor housing that provides for attachment of a multiplicity of different modules allows for enhanced ease of use by the clinician, irrespective of which module or modules are presently attached to the biosensor. In this regard, ergonomic efficiency of the biosensor housing is preserved such that usability characteristics of the biosensor are not negatively impacted when different modules are attached to the biosensor.

According to other embodiments, a modular electronic biosensor includes a housing configured for hand-held manipulation relative to a person's body surface and a base module. The base module comprises a module interface configured to engage one of a multiplicity of detachable and interchangeable modules. The multiplicity of detachable and interchangeable modules typically include at least a detachable transducer module and a detachable output module. The transducer module comprises a transducer configured to sense a property of the person's body and the output module is configured to output a signal that includes transducer signal information.

The module interface preferably comprises a module connector configured to receive a connector of the detachable module and to facilitate signal transmission between the respective connectors, a mechanical retention mechanism configured to detachably and retentively engage a mechanical engagement arrangement of the detachable module, and a sealing arrangement disposed to provide sealing between the base module and the detachable module when the detachable module is attached to the base module. As previously discussed, not all of these features are required for all biosensor embodiments.

A processor is coupled to the module connector and configured to communicatively couple with each of the detachable and interchangeable modules when attached to the base module. The housing is preferably configured to facilitate preservation of ergonomic efficiency for enhancing ease of use and hand-held manipulation of the biosensor by a clinician relative to the person's body surface after attachment of the detachable module to the base module.

In accordance with other embodiments, an electronic biosensor includes a housing configured for hand-held manipulation relative to a person's body surface, and a transducer supported by the housing and configured to sense a property of the human body, such as a manifestation of acoustic energy produced by matter of biological origin. The biosensor further includes a signal processor having an input coupled to the transducer that receives the transducer signal information. A processor is coupled to the transducer and the signal processor. Alternatively, the signal processor may be incorporated as part of the processor.

The signal processor comprises a multiplicity of channels each coupled to the input, such as at least a first channel and a second channel each coupled to the input. Each of the multiplicity of channels may be coupled to different components or devices and have disparate channel characteristics. Each of the first and second channels can be allocated for communicating with different components or devices, and each of the first and second channels may be independently controlled. For example, the first channel may be coupled to a loudspeaker and the second channel may be coupled to an external device, such as a laptop, PC, or a medical system. The biosensor according to this embodiment may, but need not be configured to incorporate modular aspects of other embodiments. For example, a unitary biosensor that does not include a module interface of a type discussed herein may provide enhanced usability by incorporating a multiple-channel signal processor of the present invention.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 11B shows a portion of a headset that incorporates a custom flex band in accordance with embodiments of the present invention;

FIG. 11C illustrates a speaker configuration in which dual speakers are mounted in the headset proximate the u-shaped portion of the headset in accordance with embodiments of the present invention;

FIGS. 12A-12C illustrate an embodiment of an electronic stethoscope of the present invention that allows for convenient installation and replacement of various types of modules in accordance with embodiments of the present invention;

Figure 1:
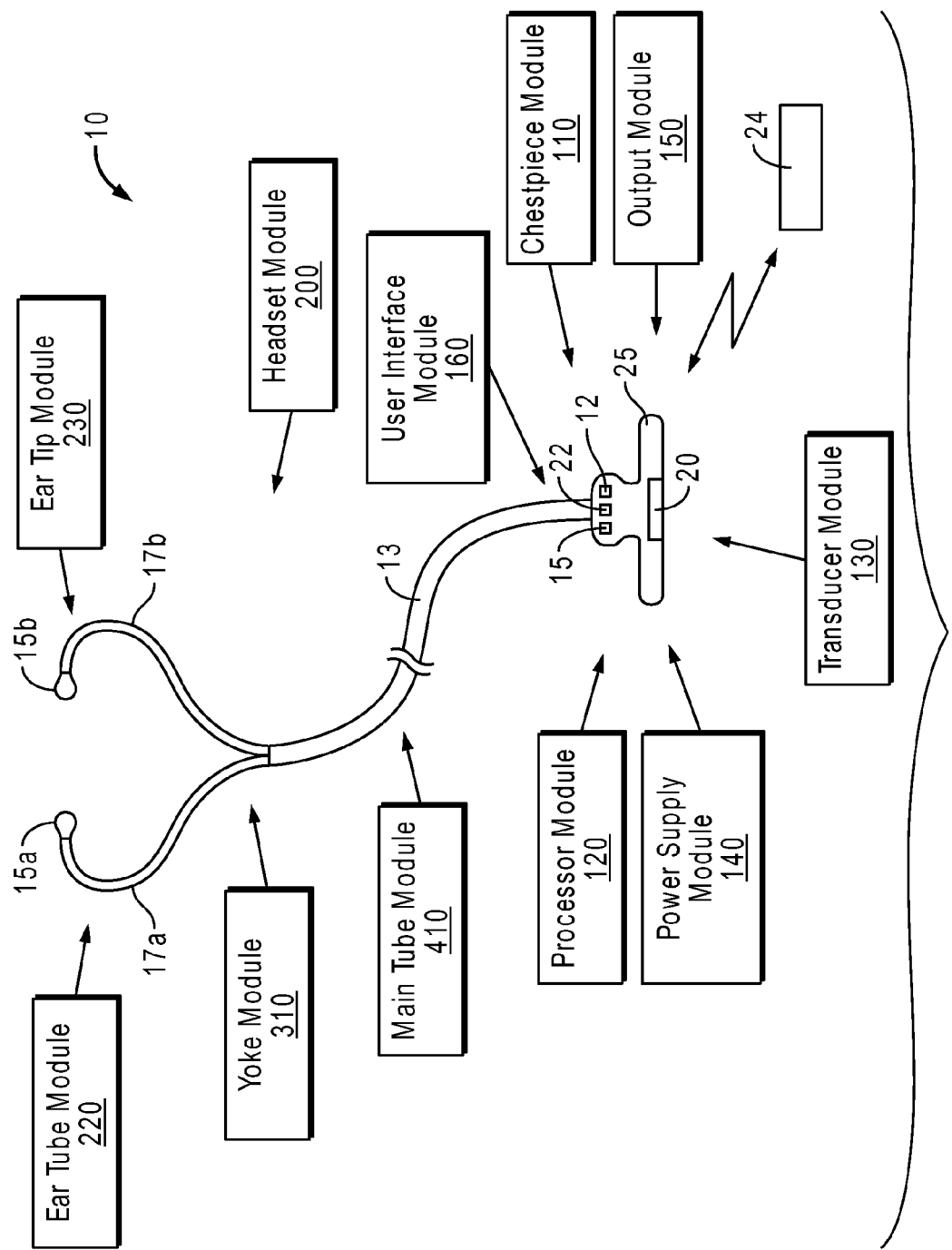
FIG. 1 shows an electronic biosensor in the form of an electronic stethoscope that includes a number of components that may be modularized in accordance with the present invention.

While the invention is amenable to various modifications and alternative forms, specifics thereof have been shown by way of example in the drawings and will be described in detail. It is to be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION OF EMBODIMENTS

In the following description of the illustrated embodiments, reference is made to the accompanying drawings that form a part hereof, and in which is shown by way of illustration, various embodiments in which the invention may be practiced. It is to be understood that the embodiments may be utilized and structural changes may be made without departing from the scope of the present invention.

Aspects of the present invention are directed to a modular approach to configuring an electronic medical device or system that incorporates one or more components that may communicatively couple to other system components or components of other devices and systems, such as by wireless or wired connections or links. Aspects of the present invention are directed to a modular approach to configuring an electronic medical system that incorporates one or more components that may be physically connectable and/or interchangeable with respect to other system components or components of other devices and systems.

In accordance with various embodiments, a modular electronic stethoscope system or other biosensor system of the present invention includes hardware and software components with standardized interfaces (e.g., "plug and play" connectivity). The biosensor or stethoscope, itself of modular design, may be part of a larger, modular system including standard elements for analysis, display, and information management. Biosensor or stethoscope modules may also be used as the foundation for other portable diagnostic devices.

Traditional stethoscopes, for example, are sold into a variety of medical markets, with each market presenting its own technical and marketing requirements. The needs of these various markets has traditionally been met by a set of distinct product designs, with relatively few shared components. It would be highly desirable to provide existing and new stethoscope markets with specialized new products. A modular approach to configuring a electronic stethoscope advantageously facilitates efficient development of new products and expedites the advancement and technological evolution of electronic stethoscopes and other biosensors.

A modular approach to configuring biosensors, such as stethoscopes, in accordance with the present invention also provides support for a "personal stethoscope" business model, in which end customers may configure a stethoscope according to their needs using standardized modules. In this regard, a modular approach to electronic stethoscope assembly provides for multiple product offerings using a common platform. Design verification, troubleshooting, and repair of stethoscope products may also be streamlined, since these functions could be implemented on a more incremental, module-by-module basis. The standardized modules may be in the form of mechanical/structural, electrical/electronic or communications modules, or a combination of these forms.

Modular design approaches of the present invention offer the potential of shortening the timelines for product upgrades once a common "base" design approach has been established. While still requiring validation of the fully integrated product, pre-existing verification of key modules could significantly accelerate the new product introduction process. Modular design approaches of the present invention may also facilitate an improved manufacturing infrastructure that would augment a "build to order" strategy and customization of stethoscopes.

A modular design approach of the present invention allows for the use of disposable modules, such as a modular chestpiece that is used to contact a patient that has or may have contagious pathogens. Modular communications and/or electronic components, for example, may facilitate easy modification of the manner in which the stethoscope operates and/or interacts with external devices and systems. An electronics or communications module, for example, may be replaceable with other such modules that provide for different functionality and compatibility with a variety of external devices and systems.

A modular medical system of the present invention may be implemented for a wide range of medical diagnostic and/or therapy devices (many of which are collectively referred to herein as biosensors). Many types of medical devices may be implemented in accordance with the present invention, particularly those configured for auscultation, and may be configured to be sensitive to sounds produced by the heart, lungs, vocal cords, or other organs or tissues of the body, for example. Although the embodiments described herein are generally directed to medical diagnostic devices that sense sounds produced by matter of biological origin, it is understood that a modular approach to implementing a medical device in accordance with the present invention is not limited to stethoscopes and other auscultation devices. Representative devices include those configured to sense a manifestation of energy produced by, or resulting from interaction with, matter of biological origin.

According to various embodiments, a modular electronic stethoscope of the present invention may be implemented to be preferentially sensitive to a range of frequencies associated with human hearing. It is understood, however, that frequencies associated with body sounds below and/or above the auditory range of frequencies may also be sensed by an electronic stethoscope of the present invention. For example, a modular electronic stethoscope of the present invention may incorporate one or more sensors implemented to sense body sounds that have frequencies ranging between just above DC and about 25 kHz.

A modular electronic stethoscope of the present invention may incorporate one or more sensors configured to produce an audible output that falls within the auditory frequency range, and may also produce sensor signals that include content above and/or below the auditory frequency range (e.g., output from an ultrasound sensor). The electronic stethoscope may include signal processing circuitry and software that performs frequency-shifting or other signal processing to utilize signals developed by sensors whose range is beyond that of the human auditory system. Such circuitry and software may also be configured to produce data of analytical value.

Embodiments of a modular electronic biosensor of the present invention include a housing comprising a base module having at least one module interface configured to engage at least one of a multiplicity of detachable modules. The module interface of the biosensor includes a module connector configured to receive a connector of a detachable module to facilitate signal transmission between the biosensor and the module. A mechanical retention mechanism is configured to facilitate detachable and retentive fixation of the detachable module to the biosensor. A sealing arrangement is preferably disposed to provide sealing at the module interface when the detachable module is attached to the biosensor. A processor is coupled to the module connector and configured to communicatively couple with the detachable module when the detachable module is attached to the biosensor. In preferred embodiments, the housing is configured to preserve ergonomic efficiency for facilitating hand-held manipulation of the biosensor relative to a person's body surface after attachment of the detachable module to the biosensor.

In some embodiments, the processor is disposed in the base module of the biosensor. In other embodiments, the processor is disposed in the detachable module or is distributed between the base module and the detachable module.

In one embodiment, a first module interface of the base module is configured to engage a detachable transducer module and a second module interface of the base module is configured to engage a detachable output module. In another embodiment, the base module supports one or more transducers and the module interface of the base module is configured to receive an output module, a power module, and interface module, or other type of module. In some embodiments, either the base module or a detachable module incorporates an ultrasound sensor or a Doppler ultrasound sensor. In other embodiments, either the base module or a detachable module incorporates a multi-dimensional sensor, such as an ultrasound imaging sensor or thermal imaging sensor.

The biosensor may be configured to communicatively couple to a headset, such as a wired or wireless headset, that is coupled to the transducer of the biosensor via an appropriate interface. For example, a military helmet may be implemented to incorporate a wireless headset configured to communicate with the biosensor. The biosensor may be configured to communicatively couple to a hearing aid via a wired or wireless connection. The biosensor may incorporate a user interface, such as one that includes a display provided on at least one of the base module and the detachable module.

One or more radios may be incorporated in the base module of the biosensor, a detachable module, or both the base module and the detachable module. The base module and/or the detachable module may comprise memory for storing software that configures the one or more radios.

In other embodiments, a first module interface may be configured to engage a detachable output module, and at least one of the detachable output module and the base module comprises a power interface configured to facilitate connection between the biosensor and an external power source, such as a stationary or portable power supply. The biosensor may include a primary power source and a secondary power source. The primary power source may be disposed in the base module and the secondary power source may be disposed in the detachable module.

The biosensor may comprise a signal processor having an input that receives the transducer signal information and at least a first channel and a second channel each coupled to the input. The first channel may be coupled to a loudspeaker via the biosensor processor and have first channel characteristics, and the second channel may be coupled to an external device via the biosensor processor and have second channel characteristics differing from the first channel characteristics. For example, the first channel may comprise an analog channel and the second channel may comprise a digital channel.

In accordance with other embodiments, a biosensor need not have a modular configuration or may have a relatively simple modular feature, such as an input/output interface (e.g., a unitary biosensor having a communication port) or an attachable power supply. In such embodiments, the biosensor may advantageously incorporate a signal processor having a multiplicity of channels having different programmable characteristics for processing transducer signal information in different ways for different purposes or different end devices or components.

Turning now to FIG. 1, there is shown an electronic stethoscope which includes a number of components that may be modularized in accordance with the present invention. Various features of the electronic stethoscope 10 illustrated in FIG. 1 may be incorporated in standardized modules that allow for a high degree of selectability as to the form and function of an electronic stethoscope. As is shown in FIG. 1, the electronic stethoscope 10 includes a pair of ear tips 15a, 15b, ear tubes 17a, 17b, and a main tube 13. The main tube 13 is coupled to a main housing or chestpiece 25, within which at least one sensor 20 is disposed. Sensor 20 is configured to sense a manifestation of energy produced by, or resulting from interaction with, matter of biological origin. For example, sensor 20 may be configured to sense sounds produced by matter of biological origin, such as sounds produced by the heart, lungs, vocal cords, or other organs or tissues of the body. Other components that may be disposed in the main housing 25 include a power source, signal processing circuitry, and a communications device.

In accordance with a modular assembly approach of the present invention, the features of the electronic stethoscope 10 discussed above may be incorporated into standardized modules. For example, the ear tips 15a, 15b, ear tubes 17a, 17b, and main tube 13 may be incorporated in a headset module 200. A number of different headset module configurations may be implemented to accommodate a variety of user needs (e.g., conventional binaural, consumer headsets, ear buds, special headsets, such as military helmet systems). Properties of a stethoscope headset that may be altered according to user need include, for example, size, length, shape, function, performance, features, durability, fidelity, color, materials of construction, engravings or markings (e.g., customer or company name, serial number), among other properties.

Components of the headset module 200 may be modularized. For example, the headset of the electronic stethoscope 10 may be assembled using a main tube module 410, a yoke module 310, an ear tube module 220, and an ear tip module 230. Each of these modules may have multiple configurations and properties, such as those discussed above. For example, the main tube module 410 and ear tube module 220 may be fabricated in a variety of tube lengths, to accommodate users of various heights and sizes.

The ear tip modules 230 may be fabricated to include ear tips of varying size and shape, and may allow for customization of ear tip fit (e.g., molded ear tips made from molds taken from a particular user). Ear tip modules 230 may be fabricated to include ear tips that can be positioned over the ear, in the ear, or in the ear canal, for example. Ear tube and tip modules 220, 230 may be fabricated to facilitate acoustic, electrical or optical transmission of body sound information. For acoustic transmission, a conventional design approach may be used to fabricate the ear tube and tip modules 220, 230. For electrical or optical transmission, the ear tube module 220 may include tubes, sheaths or other insulated flexible members within which electrical conductors or optical fiber(s) can be housed. In this configuration, the ear tip module 230 would include speakers for each ear tip. In a wireless configuration, the ear tube module 220 may not be required, as the headset can communicate wirelessly with the chestpiece.

For users that have a hearing aid in one or both ears, the ear tip modules 230 may be tailored to accommodate special hearing needs of such users. For example, an ear tip module 230 may be fabricated to account for the presence of a particular hearing aid (i.e., make and model), including electronic, acoustic, and structural accommodations. By way of further example, one or both ear tips of an ear tip module 230 may simulate the performance characteristics of the particular hearing aid of a user.

A yoke module 310 may be implemented to allow for enhanced user features and stethoscope functionality. For example, a yoke module 310 may include a speaker unit, which is typically situated at the chestpiece. A speaker unit may also be incorporated in the ear tube module 220, with a common speaker for both ear tubes or a dedicated speaker for each ear tube. The yoke module 310 may be fabricated with connectors or couplers of varying shapes or sizes, allowing connection with ear and main tube modules 220, 410 of corresponding shapes and sizes. The yoke module 310 may include electronics, such as communications, processing, and user interface electronics. For example, yoke module 310 may include a connection interface configured to receive an electronic module or adapter. As is discussed below, the chestpiece module 110 may be configured to receive such an electronic module or adapter.

The electronic module may allow for enhanced communication capabilities with external devices and systems or with other components of the stethoscope. The electronic module, for example, may enable communications between the stethoscope and other physiological sensors situated in, on, or proximate the patient. For example, the electronic module may include or otherwise enable communications between the stethoscope and various local and remote devices and systems, such as PDAs, portable PCs, and network servers. The electronic module may enable wireless (e.g., Bluetooth or ZigBee communications protocol) or wired communications.

The electronic module may allow for enhanced or extended features, such as by altering or updating software or firmware of the stethoscope, or modifying or adding diagnostic modes or functions of the stethoscope (e.g., adding heart sounds filters, adding lung sounds filters, adding detection algorithms designed for detecting particular pathologies). It is understood that the yoke module 310 and/or chestpiece module 110 discussed below may provide these and other features as a stand-alone module, and that the enhancements discussed above may be implemented via wireless communication of software. In some configurations, the yoke module 310 and/or chestpiece module 110 or other memory or processor module of the stethoscope may store software for a suite of features that can be selectively enabled or disabled by command. It is contemplated that such software and commands may be communicated between the stethoscope and a remote server system (via a wired link, wireless link or a combination of both), allowing for remote interrogation and configuration of the stethoscope (e.g., filter selection and gain control).

The chestpiece 25 of the electronic stethoscope shown in FIG. 1 typically includes a processor, memory, power supply, transducer or sensor, user interface components, and communications circuitry. The signal processing circuitry of the electronic stethoscope 10 may be configured to perform a variety of functions, ranging from simple to complex. For example, the signal processing circuitry may be configured to perform relatively sophisticated analysis of bioacoustic signals received from the sensor 20, such as body sound profile matching. The signal processing circuitry may perform various forms of statistical analysis on signals produced by the sensor 20. In such configurations, the signal processing circuitry may include a digital signal processor (DSP). Alternatively, or in addition, an external system 24 may perform all or some of such signal processing and analyses. The external system 24 may include a display, sound system, printer, network interface, and communications interface configured to establish uni- or bi-directional communication with the communications device disposed in the main housing 25 of the stethoscope 10.

According to one system implementation, the electronic stethoscope 10 may be configured to communicate with a portable, wireless external system 24, such as a PDA, laptop or tablet PC, or other wireless device. The wireless external system 24 may further be configured to communicate with a local or remote server system, such as a networked server system. Information acquired by the electronic stethoscope 10 during auscultation, for example, may be transmitted to the wireless external system 24. The wireless external system 24 may process the information to provide various output data, such as a visual, graphical and/or audible representation of the information (e.g., heart rate indication, S1-S4 heart sounds), and/or diagnostic information regarding anomalous cardiac, lung, or other organ function (e.g., cardiac murmurs such as those resulting from valve regurgitation or stenosis, breathing disorders such as pneumonia or pulmonary edema) or other organ pathology.

Analyses requiring significant data or signal processing may be performed by the wireless external system 24, rather than by the processor of the electronic stethoscope 10, or by a remote server. According to one implementation, processing of information acquired by the electronic stethoscope 10 is performed by multiple system elements based on processing resources of each of the system elements. For example, the processor of the electronic stethoscope 10 may be configured to perform rudimentary functions, such as signal filtering and waveform generation that may involve sampling and/or analog-to-digital conversion, and user feedback generation, such as illumination of indicators (e.g., LEDs or text/graphics on an LCD or OLED display) or production of audible output. A PDA or other external system 24 may be configured to perform more advanced functions, such as identification of cardiac murmurs or arrhythmias using various techniques, such as template-based morphological analysis, rate or timing analysis, frequency spectrum analysis, or pattern recognition analysis, among others.

The communications device of the electronic stethoscope 10 may be implemented to establish a conventional radio frequency (RF) link that is traditionally used to effect communications between local and remote systems as is known in the art. The communication link between the communications device and external system 24 may be implemented using a short-range wireless communication interface, such as an interface conforming to a known communications standard, such as a Bluetooth standard, IEEE 802 standards (e.g., IEEE 802.11), a ZigBee or similar specification, such as those based on the IEEE 802.15.4 standard, or other public or proprietary wireless protocol.

It is understood that the electronic stethoscope 10 may be implemented to include a hardwire connector instead of, or in addition to, a wireless communications capability. In such a configuration, a conductor (electrical or optical) may be connected between the hardwire connector or port of the electronic stethoscope 10 and an appropriate connector of a patient-external system 24. The hardware connection port of the electronic stethoscope 10, and any necessary interface circuitry, may be configured to communicate information in accordance with a variety of protocols, such as FireWire™ (IEEE 1394), USB, or other communications protocol. It is understood that various hardware connection protocols allow for the transmission of power in addition to data signals (e.g., USB), and that such connections may be used to recharge an internal or modular battery source(s) of the stethoscope. Output modules 150 shown in FIG. 1 may be fabricated to facilitate wireless and/or wired communication between the stethoscope 10 and a wide range of devices and systems.

As is shown in FIG. 1, the various components and functions associated with the chestpiece 25 may be modularized in one or preferably several modules. For example, a processor module 120 may be fabricated to allow for a variety of processing capabilities ranging from simple to complex. Processor modules 120 may vary in terms of processor speed, complexity, feature set, power consumption, memory size, and signal processing capabilities, among others. A variety of separate memory modules may also be provided, that vary in terms of size and speed, for example.

Power supply modules 140 may be designed to provide the requisite power for a particular stethoscope build configuration. As the configuration of the stethoscope is changed over time, for example, the power supply module 140 may be changed to accommodate the power supply requirements of each configuration change to the stethoscope. Power supply modules 140 may differ in terms of chemistry, form factor, rechargeability, and capacity, for example. Power supply modules 140 may be fabricated to provide a single power source or multiple power sources. For example, a primary power source may be implemented as the main source of power for the electronics of the stethoscope. A secondary power source may be a storage capacitor or battery smaller than the primary power source, and used for powering sensors or circuitry during sleep mode or for detecting conditions for transitioning the stethoscope from sleep mode to operational status.

The sensor 20 of an electronic stethoscope 10 of the present invention preferably incorporates a transducer that is configured to modulate or generate an electrical signal in response to deformation of the transducer. Suitable transducers are those that incorporate piezoelectric material (organic and/or inorganic piezoelectric material) such as piezoelectric film, piezoresistive material, strain gauges, capacitive or inductive elements, a linear variable differential transformer, and other materials or elements that modulate or generate an electrical signal in response to deformation. The transducer may be planar or non-planar, such as in the case of a curved or corrugated configuration. Suitable piezo materials may include polymer films, polymer foams, ceramic, composite materials or combinations thereof.

Additionally, the transducer may incorporate arrays of transducers of the same or different transducer type and/or different transducer materials, all of which may be connected in series, individually, or in a multi-layered structure. Suitable transducers that incorporate plural sensing elements having differing characteristics and/or sensors with tailorable sensing characteristics are disclosed in commonly owned U.S. Published Patent Application Nos. 2007/0113649 and 2007/0113654, each of which is incorporated herein by reference.

A variety of transducer modules 130 may be fabricated for easy coupling to the chestpiece. Transducer modules 130 may be varied in terms of transducer technology, as discussed above, function, size, and sensitivity, among other characteristics. A non-exhaustive list of different transducer modules 130 that may be incorporated in a modular stethoscope of the present invention include those that incorporate a heart or lung sounds transducer, an ultrasound transducer, a plethysmography sensor, electrocardiogram sensor, pulse oximeter, among others. By way of example, a transducer module 130 may incorporate an ultrasonic imaging transducer or a Doppler ultrasonic transducer that can be used for a variety of diagnostic purposes, including blood flow and blood pressure evaluations, vessel patency evaluations, and structural and/or functional evaluation of organs.

A user interface module 160 may be fabricated to provide a wide range of user interaction with the stethoscope 10. User interface modules 160 may be implemented with various types and combinations of user input features, such as buttons, keys, thumbwheels, a joystick or other known input device. User interface modules 160 may be implemented with various types and combinations of displays, ranging from LED arrays to LCD or OLED displays. One or more interface modules 160 may be situated at various locations on the stethoscope, including one or more of the chestpiece 25, the yoke, and the main tube 13, for example.

A user interface module 160, according to one embodiment, may be configured to include one or more LEDs that can provide the clinician with various information. For example, incorporating a perceptible indication of the electronic stethoscope's operating status, such as by use of one or more flashing LEDs, can further provide the clinician valuable information. Information that can be conveyed to the clinician by one or more LEDs or other visual indicators may include the power status of the stethoscope (e.g., an ON indication after automatic power-on activation), the filter mode currently being used, the status of a wired or wireless communication link, and signal strength of the transducer signal, among other types of information. For example, illumination of an LED or transition from one color to another (e.g., from red to green) may indicate automatic activation of power circuitry of the stethoscope. Flashing of the LED in a particular manner may indicate the particular filter mode selected or currently being used.

Moreover, controlling the rate of the flashes (e.g., once per 6 or 10 seconds) may allow the clinician the ability to use the flashes on the stethoscope, instead of a second hand on a watch, when determining heart rates. For example, the clinician may count heart rates between flashes and then multiply the results by 6 or 10 depending on the selected or programmed flash rate. Multiple LEDs may be used to convey different information to the clinician. Alternatively, a single LED may be used to convey multiple types of information to the clinician. One or more LEDs may be situated at a single location of the electronic stethoscope or at multiple locations.

Table 1 below provides an non-exhaustive non-limiting listing of LED illumination scenarios that may be implemented by a user interface module 160 to convey valuable information to the clinician.

TABLE 1

| LED State | Stethoscope State |
|---|---|
| Flashing 1/10 or 1/6 sec | Scope on (Also timer for manually taking pulse rate) |
| LED off | Scope off |
| Flash at low rate or unique color | Low pass filter (Bell) |
| Flash at high rate or unique color | High pass filter (Diaphragm) |
| Flash both sides or alternate sides of 'split ring switch' listed above. | Special ($3^{rd}$) filter applied |
| Unique flash rate and color on LED | Visual indicate low battery |
| Remote visibility (e.g. LED on chestpiece and in yoke area) | Visual indicator pwr on/off. Fiber optic to use one light source visible in multiple areas. |

Figure 2:
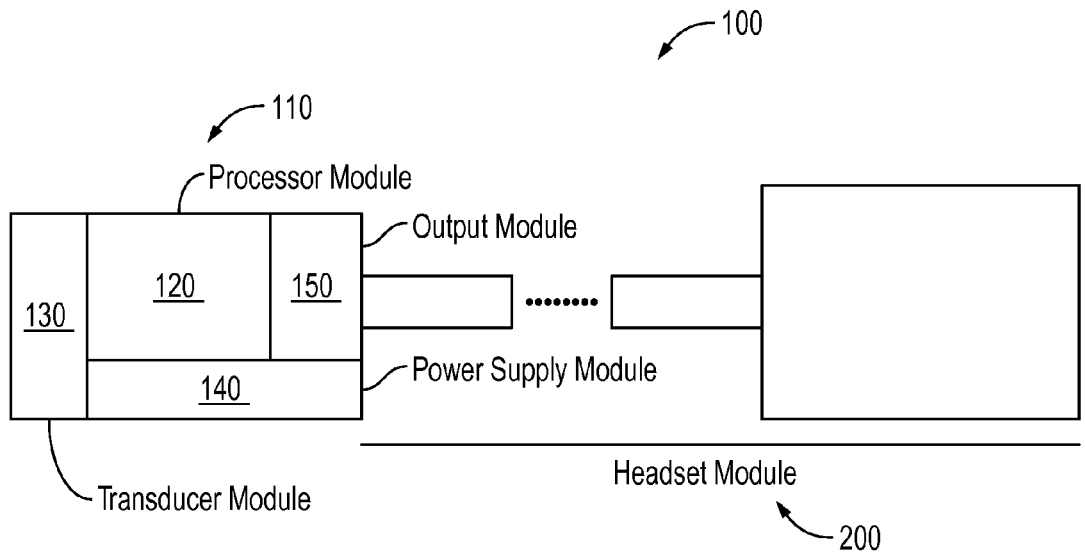
FIG. 2 is a block diagram of a modular biosensor, such as an electronic stethoscope, in accordance with embodiments of the present invention.

FIG. 2 is a block diagram of a modular biosensor, such as an electronic stethoscope, in accordance with embodiments of the present invention. The modular electronic stethoscope 100 shown in FIG. 2 includes a number of modules arranged at the chestpiece 110, which itself may be a module. A headset module 200 is depicted as being coupled to the chestpiece 110. The modules arranged at the chestpiece module 110 include a processor module 120, output module 150, power supply module, and transducer module 130. It is understood that one or more of the modules shown arranged at the chestpiece module 110 may instead be arranged elsewhere on the stethoscope, such as at the yoke.

The modular electronic stethoscope may be configured to accommodate a variety of headset and output modules 200, 150. A variety of audio output options may be provided using a different headset and output modules 220, 150. For example, binaural headset modules 200 can be constructed with a sound chamber at one of several positions (e.g., near the output module 150 on the chestpiece 110, at the yoke, or near the ear tips). The output transducer in these headset modules 200 may be configured to receive analog signals from an output module 150 in the chestpiece assembly 110. Typically, these modules may be designed to resemble the traditional headset of mechanical stethoscopes.

Consumer-style headset modules 200 may be linked to an output module 150 by analog/digital cables or by a wireless link (e.g., Bluetooth). The headsets may be equipped with active noise cancellation circuits. These may be of a general design not limited to traditional medical applications. Military-style headset modules may be linked to an output module 150 by analog/digital cables or by a wireless link. Military-style headsets may be embedded in a protective helmet and be capable of operating in extreme environments. The particular nature of the link and output module circuitry may be based on military communications standards.

Hearing aids that can accommodate wired/wireless connection to output module 150 may be employed. In some configurations, an intermediary device may be used to receive output data from the electronic stethoscope and transmit this data wirelessly to a receiver of the hearing aid. This intermediary device may be incorporated in a portable unit that is worn by the clinician or can be set on a surface in proximity to the clinician. A wired connection is typically provided between the electronic stethoscope and the intermediary device. In other configurations, no such intermediary device is needed, in which case transducer information is communicated wirelessly from the biosensor to the hearing aid's receiver. In this configuration, a wireless transmitter or transceiver may be disposed somewhere in the biosensor (e.g., the base module), the transducer module, or in the output or other module.

Multiple headset modules may be driven from a single output module (e.g., networked Bluetooth or utilize a wired hub, such as a USB hub system). Headsets could be individually powered to minimize the drive requirements for amplifiers within the output module and hub. The audio system on a PDA, PC or other local system may be considered a compatible headset module utilizing a wired/wireless communications link.

An electronic stethoscope of the present invention may be provided with an output module 150 based on a radio link, such as a software defined radio (SDR) link. A set of output modules 150, for example, may be constructed around a common SDR component, with different communications modalities (e.g., Bluetooth, Zigbee, FM) supported through the use of different software and antenna components. A more advanced output module 150 may support multiple communications modalities as selected by an associated processor module 120. Output modules 150 may also differ in terms of their power consumption and transmission range, for example. Other types of radios (e.g., FM radios, Medical Implant Communication Service (MICS) radio or cellular radio, such as a GSM/Edge radio or EGPRS radio) may be employed in the output module 150, the chestpiece 110 or other component of the electronic stethoscope. Long range radios, such as cellular radios for example, allow for long range connectivity between the biosensor and remote devices or servers via cellular infrastructure, such as a remote server that implements diagnostic software to process transducer information acquired by the biosensor.

An electronic stethoscope of the present invention may accommodate a variety of modular power supplies 140. The stethoscope may be powered from a variety of power sources utilizing a common electromechanical interface, for example. A power supply module 140 may include a compartment for a disposable battery (e.g., alkaline or lithium) accessible to the stethoscope user. Power supply modules 140 of different sizes may be used to support different battery types or incorporation of a "spare" battery. The power supply module 140 may incorporate a completely-sealed and/or high-capacity battery system to support stethoscope use in extreme environments.

Power supply modules 140 may include a rechargeable battery system in an accessible compartment, with the batteries removed by the user for insertion on an external battery charger system. Power supply modules 140 may provided with an electromechanical interface for a line-powered charging stand. Charging may be performed with or without removal of the power supply module 140 from the stethoscope. In one implementation, a power supply module 140 may include a capacitor or battery that is rechargeable by turning a crank that turns a dynamo coupled to the capacitor or battery. Such a power supply module 140 may incorporate an integral crank or a socket that receives a detachable crank. Such an arrangement may be located on the yoke or the chestpiece. Alternatively, an energy harvesting unit may be incorporated in a power supply module 140 that is configured to harvest kinetic energy generated when moving the biosensor and convert this kinetic energy to electrical form that can be stored and used by the electronic stethoscope.

An electronic stethoscope of the present invention may be provided with modular processors 120. A variety of modular stethoscopes may be based on the use of different processor modules 120 providing a range of software and user control and display functions. The processor modules 120 may have standard interfaces for effecting connectivity and communication with a variety of transducer modules 130, output modules 105, and power supply modules 140. Processor modules 120 of the present invention may incorporate different processors to provide a range of functionality based on their particular CPU, memory, and software configuration.

The design of the user interface or user interface module (such as shown in FIG. 1) may vary according to the functionality supported by the module and the sophistication/needs of the intended user. Software drivers may be used to provide required protocols for interfacing with specific output and transducer modules.

An electronic stethoscope of the present invention may be provided with modular transducers 130. An electronic stethoscopes may accommodate transducer modules that are based on traditional transducers, such as an acoustic or motion (e.g., acceleration) sensor. The response properties of such transducers can be altered by mechanical prefilters (e.g., diaphragms), resonant chambers, and mounting systems, which may be modularized or incorporated into the transducer module 130. The sensitivity to ambient noise can be affected by the use of multiple acoustic pathways which provide opportunities for phase-cancellation.

A variety of transducer modules 130 may be provided, each designed around a particular set of signal and noise spectra. For example, one could optimize transducer modules 130 for specific applications. Such applications may include detection of lung sounds within a hospital environment characterized by ventilator noise, detection of heart sounds within an air-ambulance environment (dominated by the noise from helicopter blades), and detection of carotid artery sounds in a quiet examination room, for example. Transducer modules 130 may be interchangeable (like the lenses on a single-lens reflex camera) and rapidly mounted and dismounted, as in the case of bayonet systems.

The identity of the transducer module 130 and any other module of the stethoscope is preferably coded for electronic recognition by the processor module of the stethoscope 100. For example, a small memory device may be used for each module that uniquely identifies each module. Configuration information (hardware and software) may be read by the processor module 120 when a particular module is connected (or modified) to the stethoscope 100. In response to the configuration data, the processor module 120 may modify various operating parameters of the stethoscope 100. For example, configuration data indicating that a different transducer module 130 has been connected to the stethoscope 100 may result in a mode change in the processor module 120. Such mode changes may involve one or more of changes in filter and/or gain parameters, use of different input/output or communication protocols, use of different signal processing and detection/analysis algorithms, and changes in user interface functionality, such as different display modes or LED annuciator sequencing, for example.

As discussed hereinabove, the transducer module architecture of an electronic stethoscope 100 of the present invention may be generalized and applied to other potential diagnostic devices. A more generalized architecture may include components for both emitting and receiving energy, as in the case of the following illustrative examples. Ultrasound transducer modules 130, such as ultrasonic Doppler modules for example, require both an ultrasound transmitter and a receiver, together with significant signal processing elements, which could be provided by an appropriately configured processor module 120. An infrared transducer module 130 for tissue perfusion and/or oxygen-saturation detection may utilize an infrared-emitting diode and a sensitive photodetector. A transducer module 130 that incorporates a non-contacting heart sound monitor for burn victims may utilize a laser diode and photodetector. A transducer module 130 that incorporates a non-contacting heart monitor for personnel in military protective gear or hazmat suits may utilize low-power RF or microwave radiation and a sensitive receiver system. An RF transmitter/receiver within a transducer module 130 may be configured to interact with a passive transducer placed on a body surface.

Figure 3:
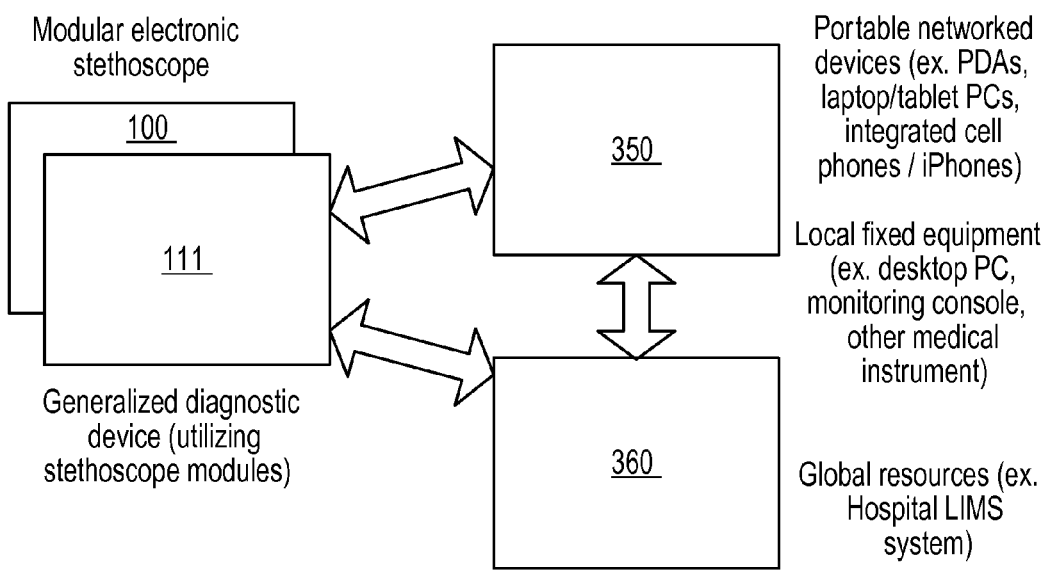
FIG. 3 is a block diagram of a modular biosensor, stethoscope or other medical diagnostic system that is part of a networked medical system in accordance with embodiments of the present invention.

As is shown in FIG. 3, a modular biosensor system, such as a stethoscope system, of the present invention or other medical diagnostic system may be based on local or global networking. A modular stethoscope 100 for other modular medical diagnostic device 111, for example, may itself be viewed as one module of a larger networked medical environment, such as a telemedicine system. This environment may include linkages between the stethoscope 100 or other modular medical diagnostic device 111, local devices 350 (e.g., PDA, PC, or another portable medical instrument), and a more global information management system 360, such as a main hospital network or remote clinic server (e.g., hospital LIMS system). The stethoscope 100 or other medical diagnostic device 111 may be designed for efficient data collection and transfer. The data analysis may be highly distributed across the system, as discussed previously.

Figure 4A:
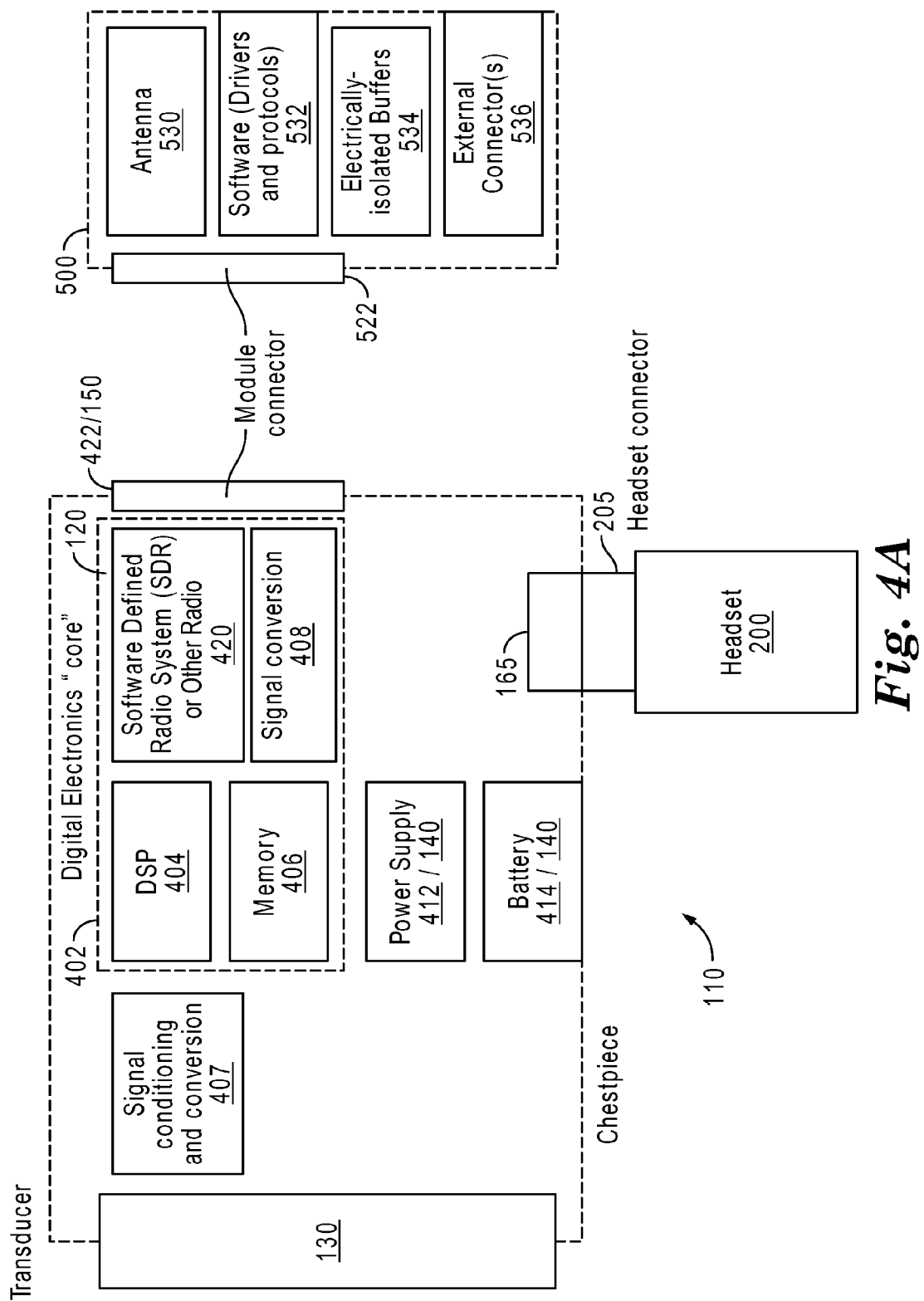
FIG. 4A is a block diagram of a modular biosensor, such as an electronic stethoscope, in accordance with embodiments of the present invention.

FIG. 4A is a block diagram of a modular biosensor, such as a stethoscope, in accordance with embodiments of the present invention. It is understood that a modular stethoscope of the present invention may be defined as including at least one modularized component. It is believed that enhanced functionality and flexibility may be achieved by provision of multiple modularized components for an electronic stethoscope. It is further understood that some of the components and/or modules shown in FIG. 4A and other figures may be located at stethoscope locations other than indicated or suggested in the figures, such as in the yoke.

The stethoscope depicted in FIG. 4A includes a core 402 of digital (and possibly analog) electronics. This core 402 of electronics may define a platform of core architecture that can be used across different families of stethoscopes. The core electronics 402 may be incorporated as a permanent unit in a stethoscope or in processor modules 120. Typical components of the core electronics 402 include a processor 404 (e.g., DSP), memory 406, signal conversion or analysis circuitry 408 (which may include or exclude analog circuitry), and a radio, such as a software defined radio system or SDR 420.

The core electronics 402 is preferably incorporated in a processor module 120 that is installable at the chestpiece 110, which may be considered a base module of the modular stethoscope. The chestpiece 110 is further shown to include signal conditioning and conversion circuitry 407, a power supply 412/140, a battery 414/140, and a transducer module 130. The power supply 412/140 may incorporate battery 414/140 or represent a power source different from the battery 414/140, as discussed previously. The chestpiece module 110 also includes a headset connector or interface 165 that coupled to a corresponding connector 205 of the headset 200. A module connector 422/150 (also referred to herein as a module interface) is provided on the chestpiece module 110 and configured to couple with a corresponding connector or interface 522 of an installable module 500.

The module connector or interface 422/150 preferably incorporates an electrical or optical connector to facilitate signal transmission between the connection interfaces of the chestpiece 110 and module 500. A mechanical retention mechanism of the chestpiece's module interface 422/150 is configured to detachably and retentively engage a mechanical engagement arrangement of the module 500. A sealing arrangement is preferably disposed to provide sealing between the chestpiece's module interface 422/150 and the connection interface of the module 500 when the module 500 is attached to the chestpiece 110. The sealing arrangement typically provides at least a splash proof level of sealing.

The configuration shown in FIG. 4A may include a conventional stethoscope headset (or a modular headset 200) while utilizing modules to define wired and wireless links to other devices. The modules 500 may be configured to provide one or both of wireless or wired connectivity with other devices and systems. The wireless mode of the assembled stethoscope is set according to the specific antenna system and software provided by the module 500. Similarly, the wired interface supported by the stethoscope is determined by the specific hardware connector(s) and software driver(s) provided by the module 500.

The connector 522 of the module 500 is placed in a corresponding connector 422 of the chestpiece module 110 in a manner which minimizes damage, while also providing sufficient mechanical support for the module 500. The modules 500 may be thin (like popular flash memory devices such as SIMM or memory sticks, especially if no external connectors are required) or thick (like popular PCMCIA cards for laptop computers which typically include one or more external connectors). As discussed previously, a seal is preferably disposed at the connection interface between the chestpiece module 110 and the detachable module 500 to protect against water ingression and other environmental contaminants.

In the configuration shown in FIG. 4A, the module 500 includes an antenna 530, software 532, such as drivers and protocols, electrically isolated buffers 534, and an external connector 536. The external connector 536 provides for wired connections to the chestpiece module 110 via the module 500.

Figure 4B:
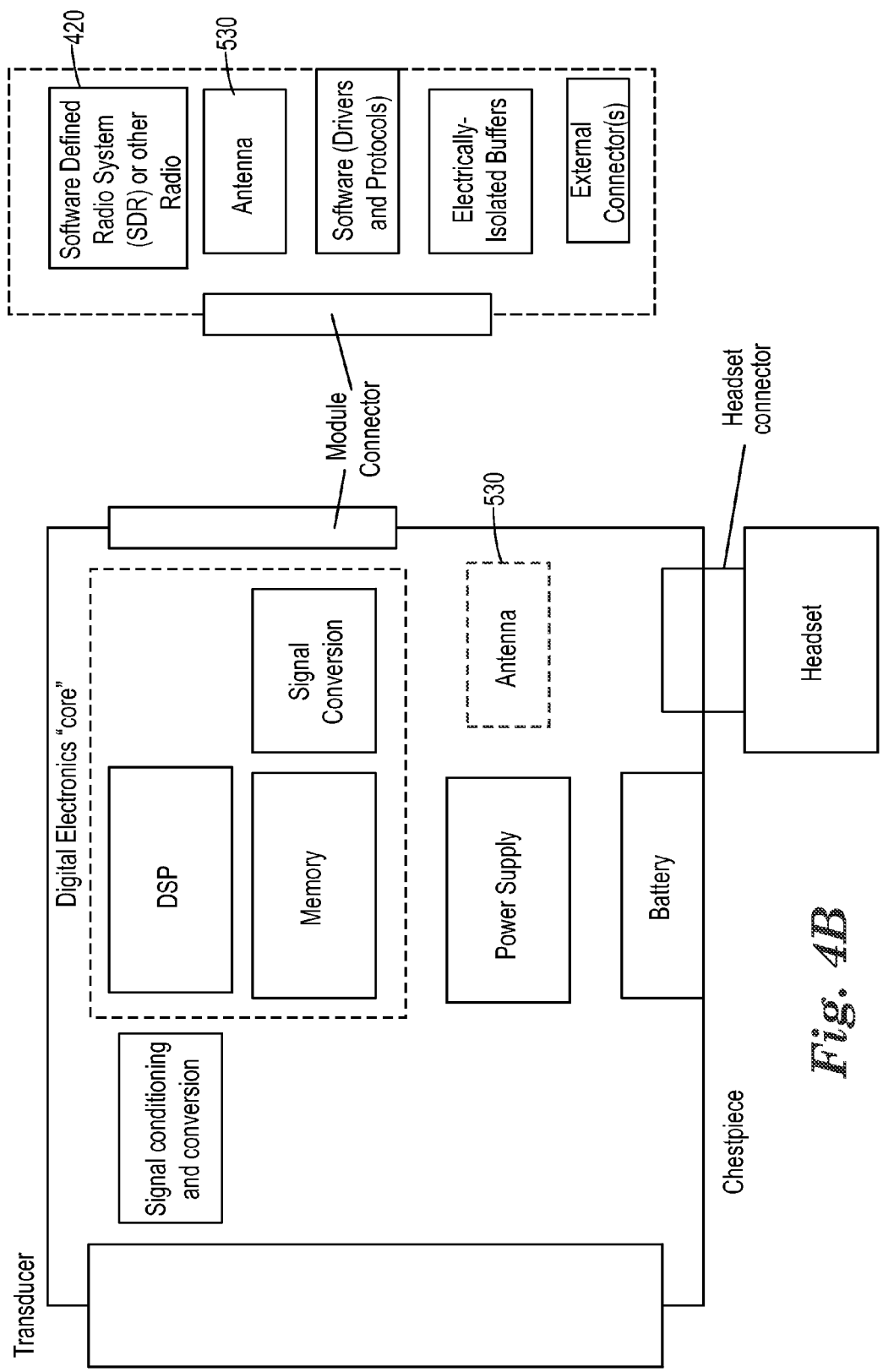
FIG. 4B is a block diagram of a modular biosensor, such as an electronic stethoscope, in accordance with embodiments of the present invention.

FIG. 4B shows a block diagram of a variation of the embodiment of FIG. 4A. In the configuration shown in FIG. 4B, the radio 420 may be incorporated as part of the module 500, rather than the chestpiece module 110. The antenna 530 may be mounted in either of the module 500 or the chestpiece module 110. In another configuration, multiple radios may be used in the stethoscope (or other biosensor). These radios may be incorporated in the chestpiece module 110, the detachable module 500, or distributed between the chestpiece module 110 and the detachable module 500. For example, a first radio may be a short range radio (e.g., Bluetooth) and a second radio may be a long range radio (e.g., GSM/Edge radio).

Figure 5A:
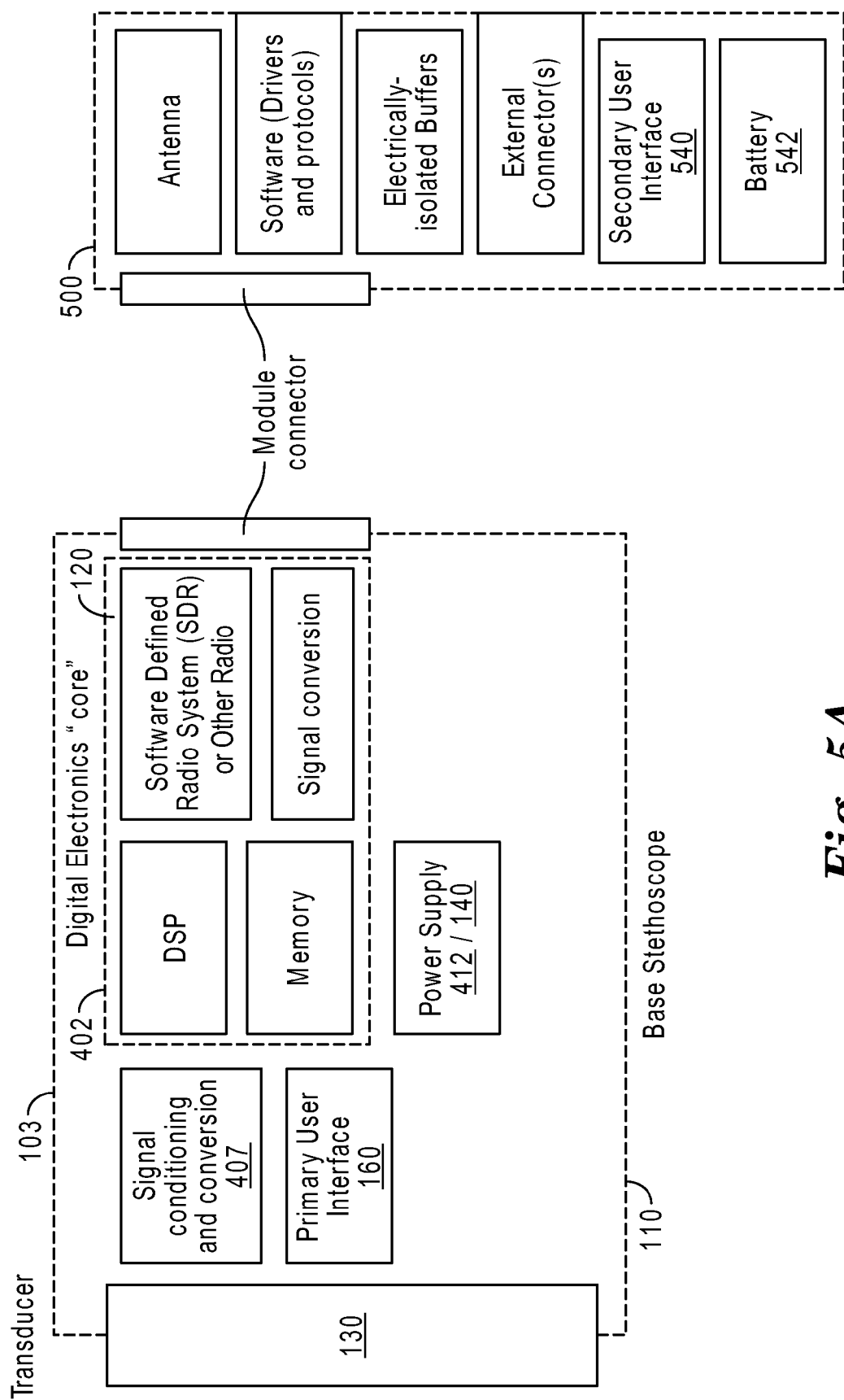
FIG. 5A is a block diagram of a modular biosensor, such as an electronic stethoscope, in accordance with embodiments of the present invention.

FIG. 5A is a block diagram of a modular biosensor, such as a stethoscope, in accordance with embodiments of the present invention. This configuration includes only a chestpiece module 110 to constitute the base stethoscope configuration and a communications module 500. Many options are available for an audio output. Such options include, for example, a wireless headset used with the module-supported radio system, a wired headset using analog output provided via an external connector (e.g., stereo audio jack) on the module, or audio could be broadcast from on a computer sound system over a wireless or USB link. As discussed previously, the wireless mode of the assembled stethoscope is set according to the specific antenna system and software provided by the module 500. Similarly, the wired interface supported by the stethoscope is determined by the specific hardware connector(s) and software driver(s) provided by the module 500.

Figure 5B:
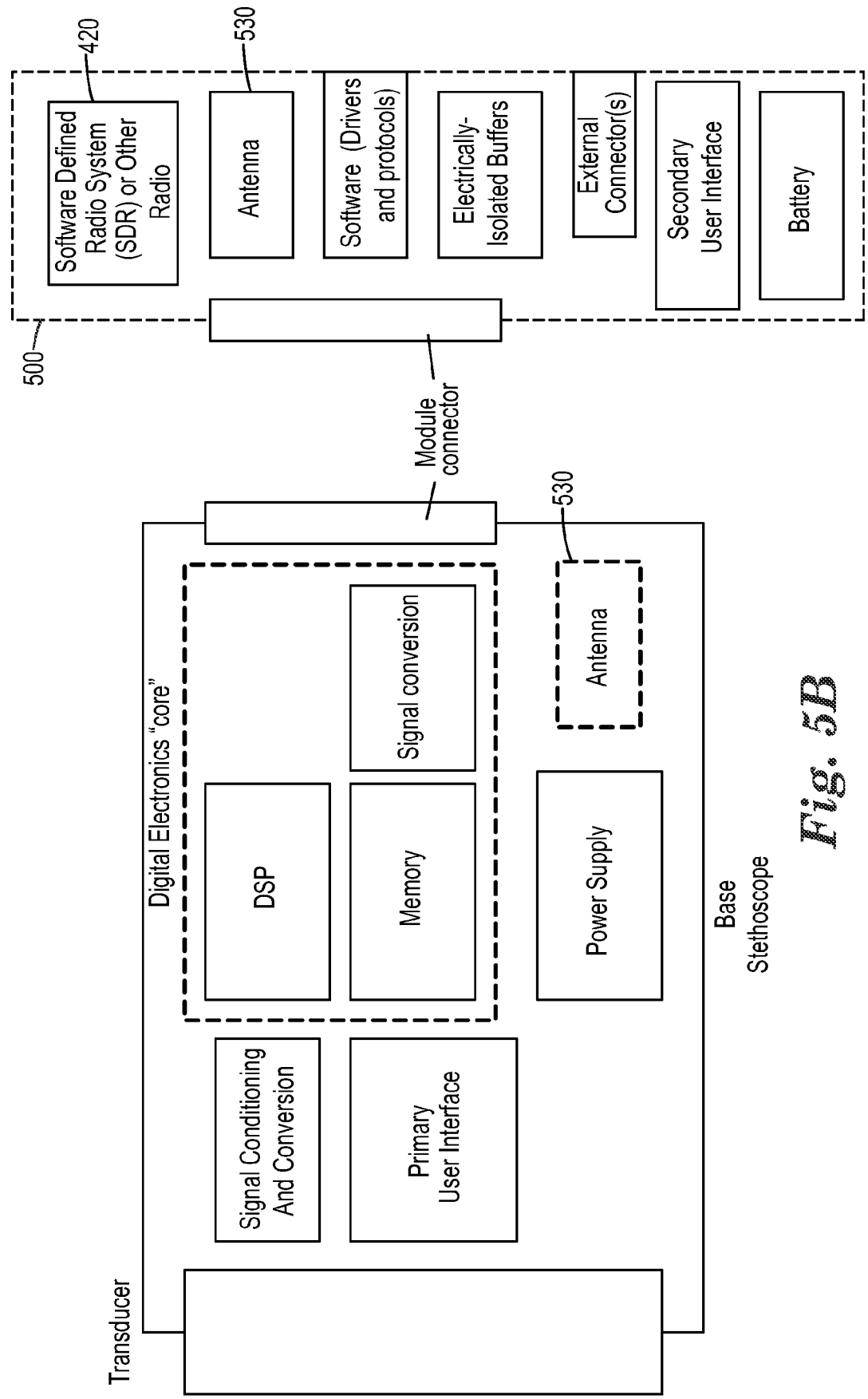
FIG. 5B is a block diagram of a modular biosensor, such as an electronic stethoscope, in accordance with embodiments of the present invention.

FIG. 5B shows a block diagram of a variation of the embodiment of FIG. 5A, in which the radio 420 may be incorporated as part of the module 500, rather than the chestpiece module 110. As in the embodiment of FIG. 4B, the antenna 530 may be mounted in either of the module 500 or the chestpiece module 110, and one or more radios may be incorporated in the chestpiece module 110, the detachable module 500, or distributed between the chestpiece module 110 and the detachable module 500.

The module 500 may also include additional indicators and/or controls as a secondary user interface 540 which expand the human interface provided directly on the chestpiece or yoke modules. Also, the module 500 may be enlarge to include a battery system 542. The battery 542 may be a disposable battery accessible via an access door on the module or a rechargeable battery sealed within the module.

Figure 6:
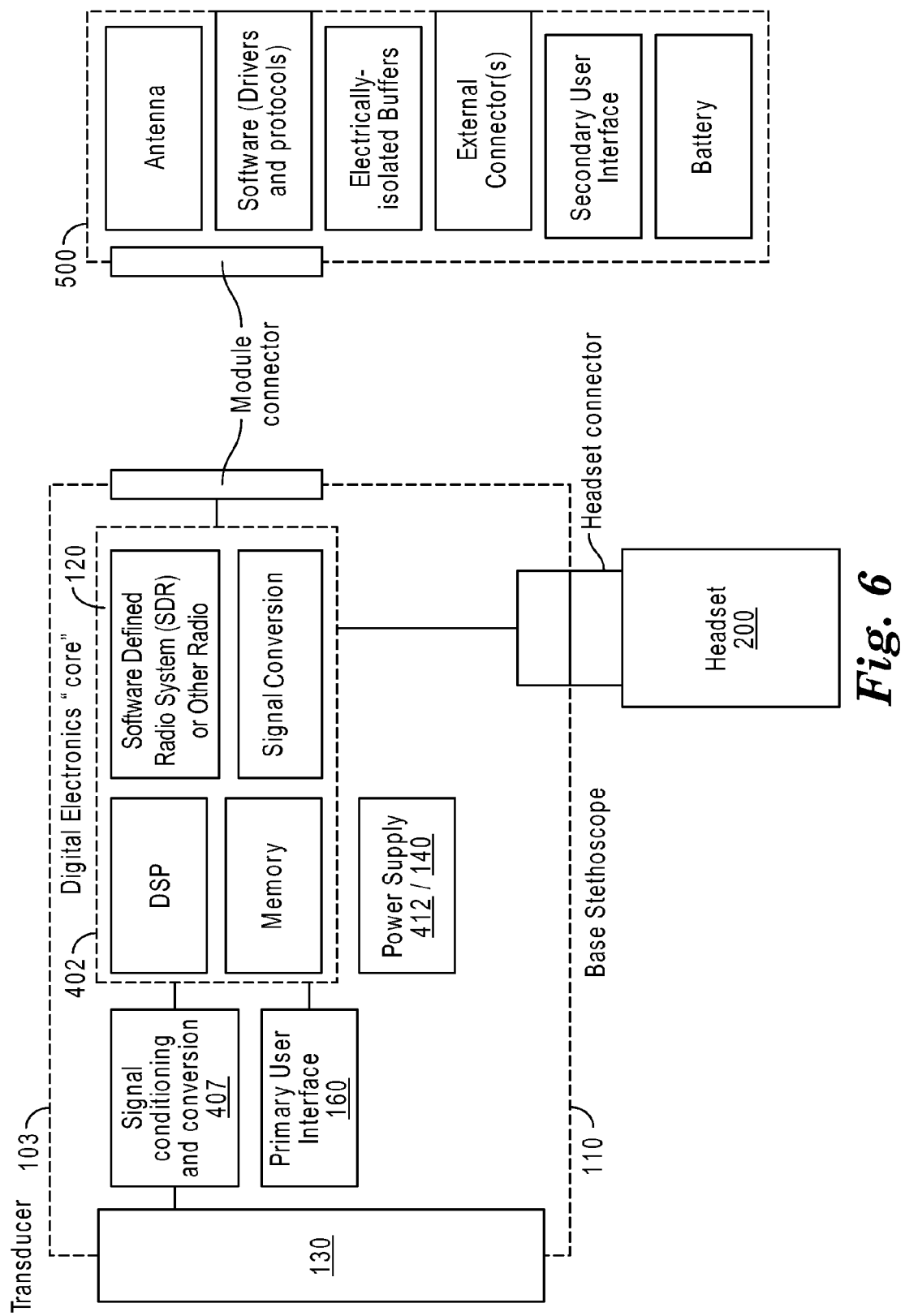
FIG. 6 is a block diagram of a modular biosensor, such as an electronic stethoscope, in accordance with embodiments of the present invention.

FIG. 6 is a block diagram of a modular stethoscope in accordance with embodiments of the present invention. The configuration illustrated in FIG. 6 is similar to that shown in FIG. 5A, but incorporates a conventional headset (which may alternatively be a modular headset 200) connected to the base stethoscope.

Figure 7:
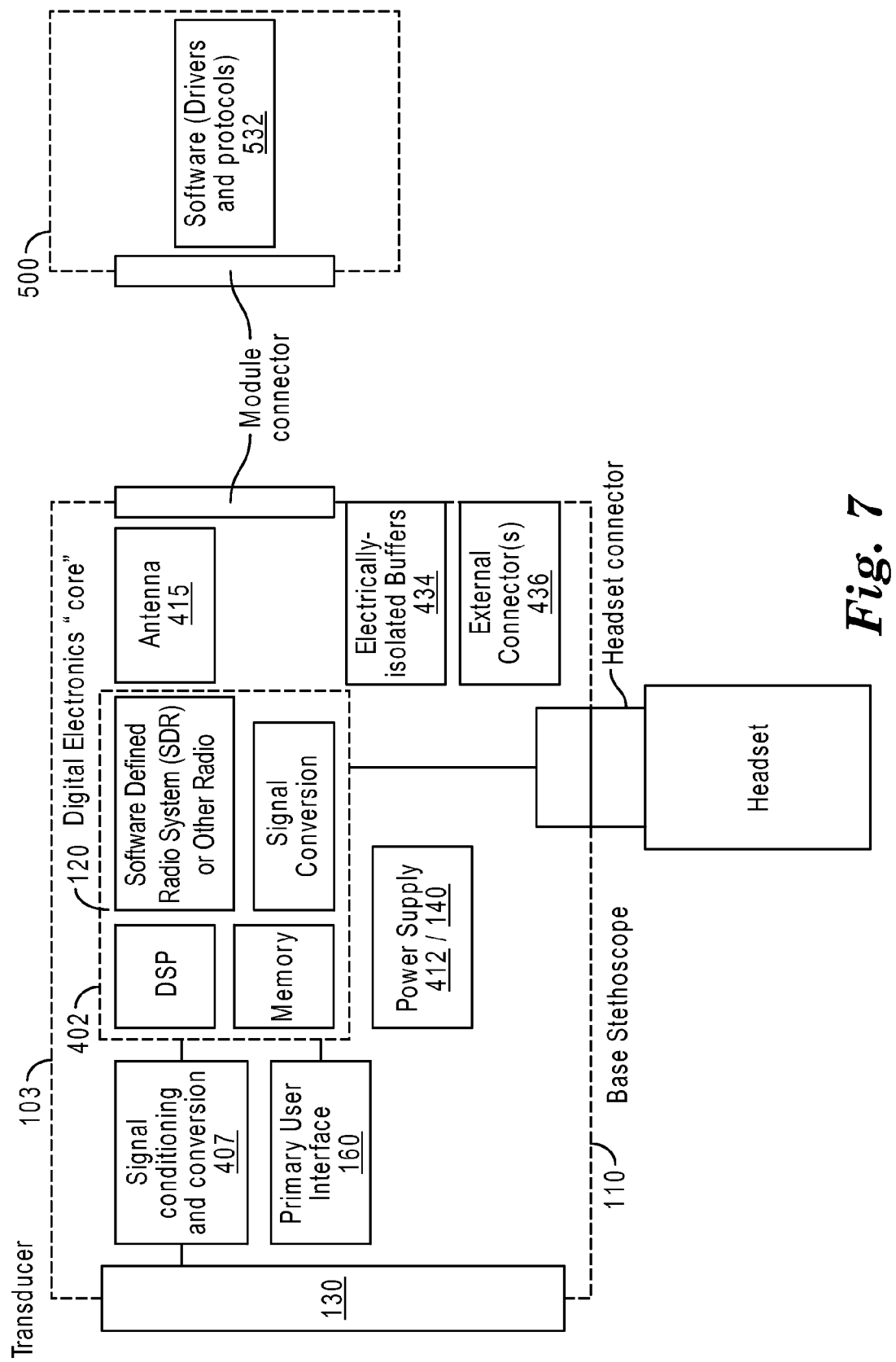
FIG. 7 is a block diagram of a modular biosensor, such as an electronic stethoscope, in accordance with embodiments of the present invention.

FIG. 7 is a block diagram of a modular stethoscope in accordance with embodiments of the present invention. The configuration illustrated in FIG. 7 places all radio components and external connectors on the chestpiece 110. The module 500 in this illustrative embodiment provides protocol and/or driver software for the various communication hardware options supported by the chestpiece 110. In this configuration, the module 500 may be extremely small, perhaps the size of mini-SMD or transFlash memory cards commonly used in cell phones.

Figure 8A:
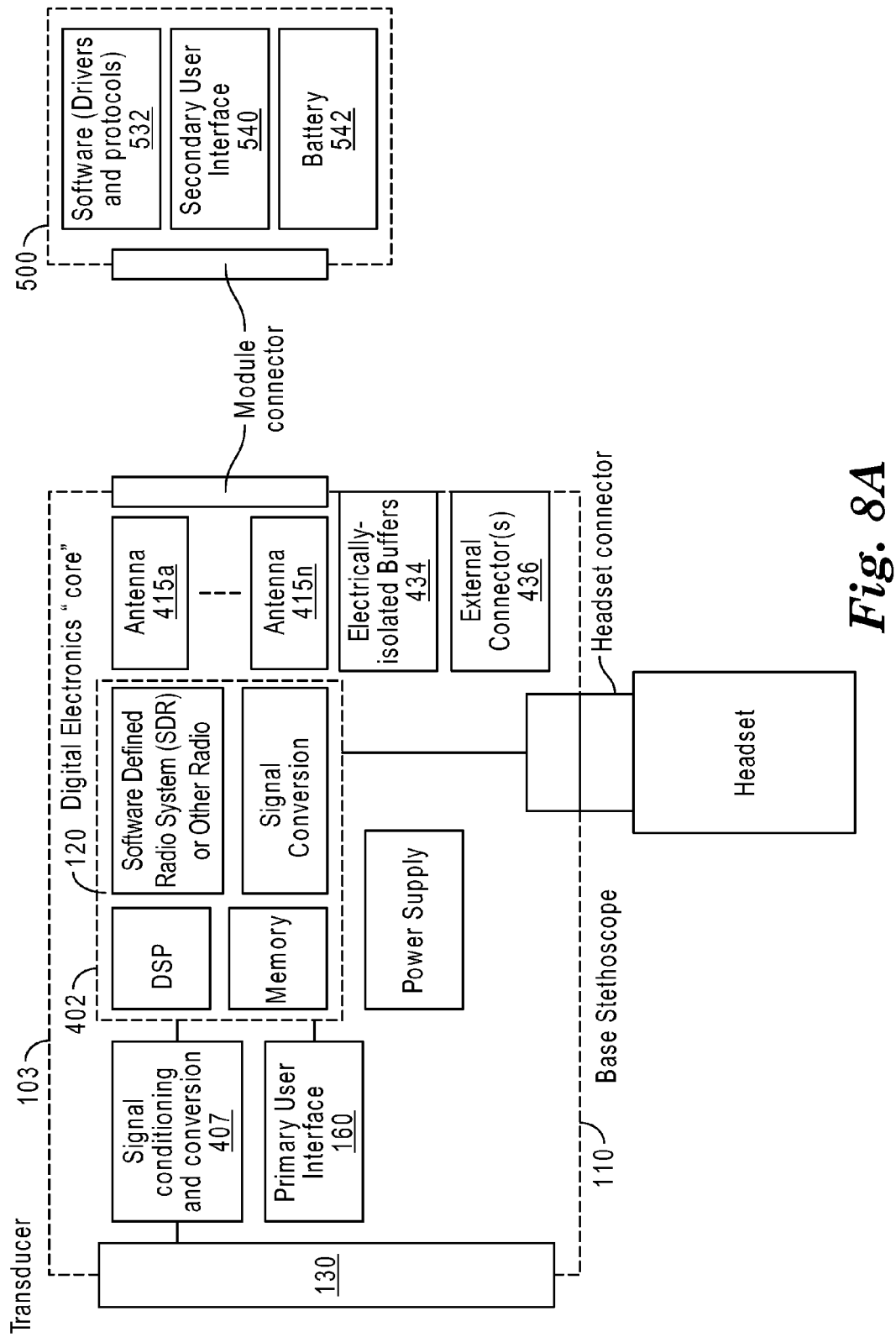
FIG. 8A is a block diagram of a modular biosensor, such as an electronic stethoscope, in accordance with embodiments of the present invention.

FIG. 8A is a block diagram of a modular stethoscope in accordance with embodiments of the present invention. The configuration illustrated in FIG. 8A assumes a chestpiece 110 populated with a wide range of multiple antennas 415a-415n and external connector options. Many of the electronic functions on the chestpiece 110 are integrated within a small number of hardware components within the chestpiece 110. Communications options may be selected and deselected by software provided by the module 500.

Figure 8B:
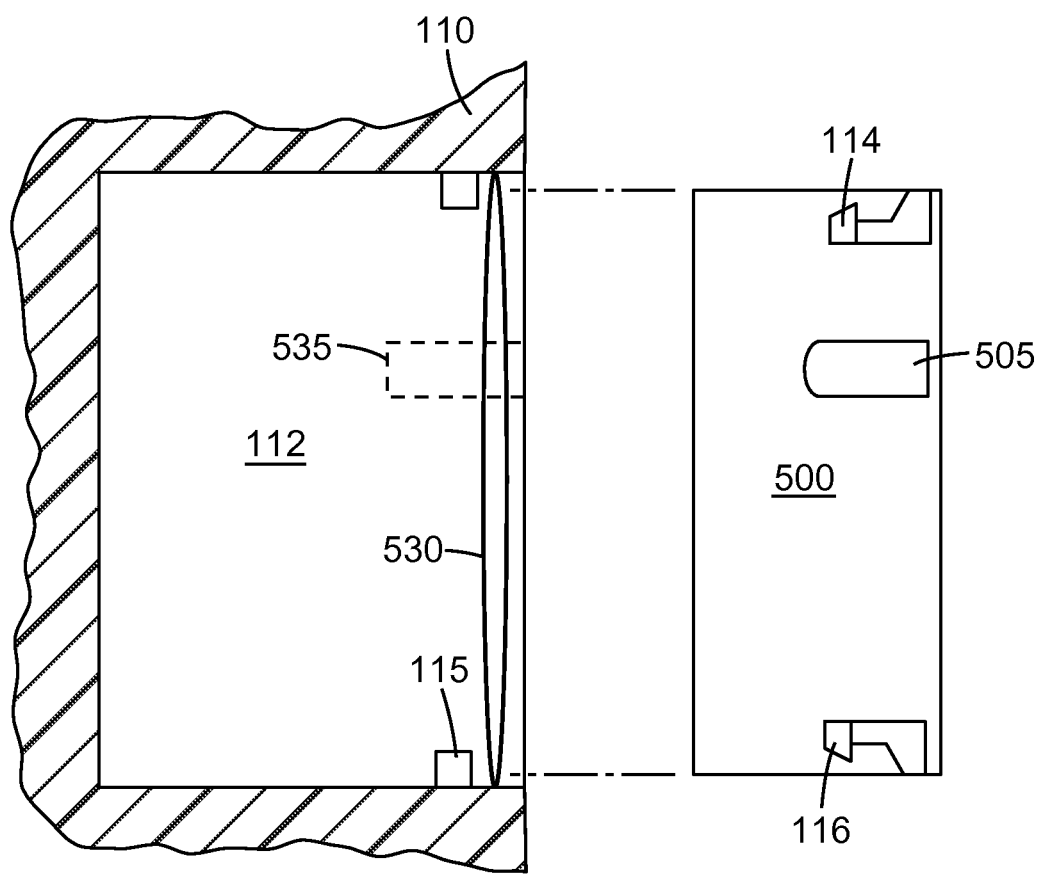
FIG. 8B shows an interface of a modular biosensor, such as a modular stethoscope, that is configured to receive one of a plurality of interchangeable modules in accordance with embodiments of the present invention.

FIG. 8B shows an interface of a modular biosensor, such as a modular stethoscope, that is configured to receive one of a multiplicity of detachable/interchangeable modules 500 in accordance with embodiments of the present invention. FIG. 8B shows a base module of a biosensor 110 (e.g., a chestpiece module 110 of a stethoscope) that includes a recess or port 112 configured to receive a detachable module 500 of a type described herein. The chestpiece port 112 includes a connector 535 that is configured to communicatively couple with a connector 505 of the detachable module 500 when the module 500 is installed in the port 112. The connectors 535/505 are typically configured with electrical connectors, but may also be configured with optical connectors. The connectors 535/505 may be hybrid connectors that include both electrical and optical connector elements. The connectors 535/505 are configured to facilitate signal transmission between the connection interfaces of the chestpiece 110 and detachable module 500.

The chestpiece port 112 and module 500 include engagement features that define a mechanical engagement arrangement that facilitates detachable retention of the module 500 within the chestpiece port 112. Various mechanical engagement arrangements may be implemented, such as snapfit engagement features 115, 116 as shown in FIG. 8B. The mechanical engagement arrangement preferably includes a keying feature that allows the module 500 to be installed into the chestpiece port 112 in a specific orientation. Other suitable mechanical engagement arrangements include a bayonet (e.g., BNC) connector or a twistable or torqueable connector with a registration/key feature, for example.

A sealing arrangement 530 is preferably disposed to provide sealing between the chestpiece 110 and the module 500 when the module 500 is installed into the chestpiece port 112. The sealing arrangement 530 preferably provides a splash proof level of sealing, but may provide less or more sealing depending on the particular device configuration and usage requirements. For example, a hermetic or near-hermetic sealing arrangement 530 may be employed for stethoscopes or other biosensors that are used in hazardous or extreme environments. Various known seals or gaskets may be employed, including o-rings for example.

Figure 9A:
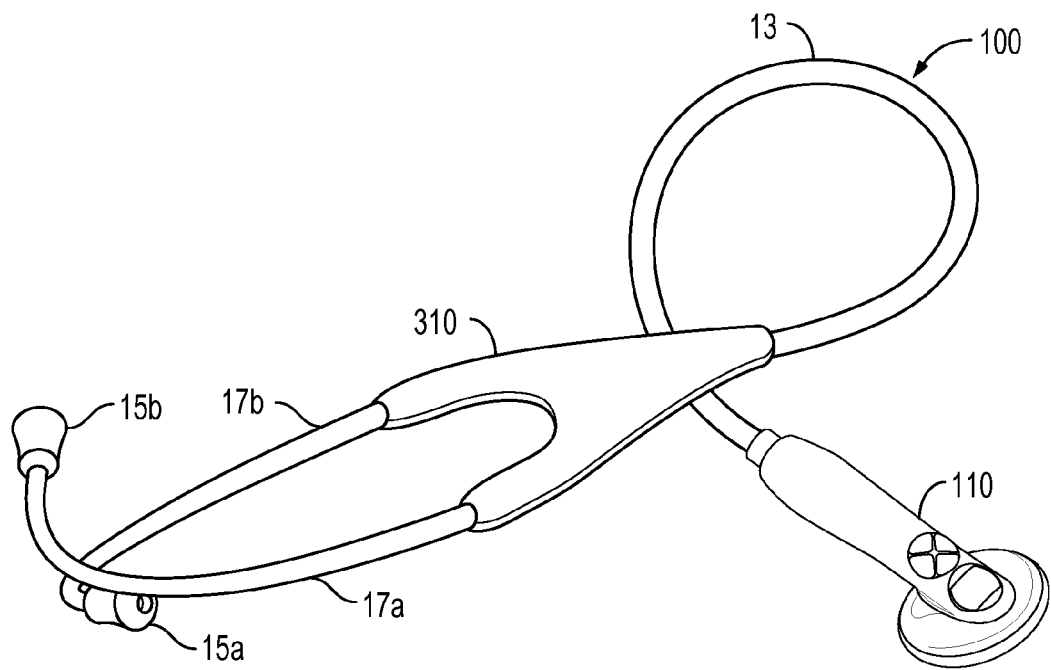
FIG. 9A illustrates a modular electronic stethoscope in a fully assembled configuration in accordance with embodiments of the present invention.

Turning now to FIGS. 9A-11C, there is shown various embodiments of a modular stethoscope in accordance with embodiments of the present invention. A modular assembly approach for an electronic stethoscope of the present invention allows manufacturers and retailers the flexibility to offer accessory kits for users who may wish to select among various features and options to suit their needs. FIG. 9A illustrates a modular electronic stethoscope 100 in a fully assembled configuration. As discussed above, many components of the modular stethoscope 100 may be modularized, allowing for a wide range of styles, functionality, and user interaction.

Figure 9B:
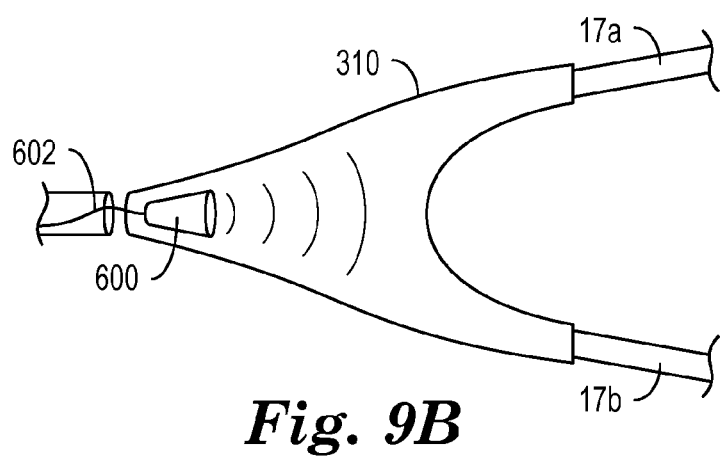
FIG. 9B illustrates a portion of a modular electronic stethoscope that includes a yoke and a loudspeaker mounted within the yoke in accordance with embodiments of the present invention.
Figure 9C:
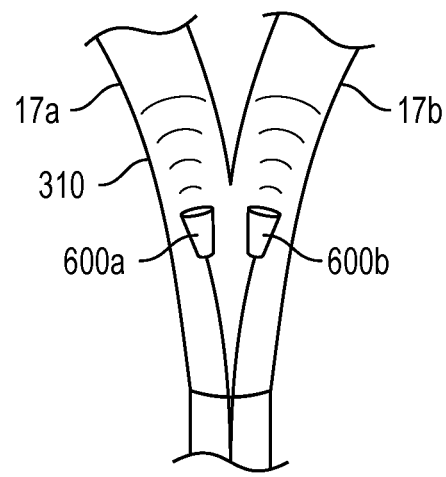
FIG. 9C illustrates a portion of a modular electronic stethoscope that includes a yoke and dual loudspeakers mounted within the yoke for separately controlling the sound (e.g., amplitude, frequency, etc.) broadcasted through respective ear tubes in accordance with embodiments of the present invention.

FIGS. 9B and 9C illustrate a yoke 310 of an electronic stethoscope that includes a speaker arrangement. In generally, the location of the speaker arrangement within the stethoscope should be selected so as to reduce or minimize the transmission of frictional noise. The yoke 310 is preferably a modular yoke. In FIG. 9B, a single speaker 600 is situated in the yoke 310 at a suitable location such that sound produced by the speaker 600 is transmitted through both ear tubes 17a and 17b. In FIG. 9C, a dual speaker arrangement is employed. In this configuration, a first speaker 600a is situated in the yoke 310 at a suitable location such that sound produced by the first speaker 600a is transmitted only through ear tube 17a. A second speaker 600b is situated in the yoke 310 at a suitable location such that sound produced by the second speaker 600b is transmitted only through ear tube 17b. In an alternative arrangement, speakers 600a and 600b may be mounted within ear tubes 17a and 17b, respectively.

As previously discussed, the speakers 600a, 600b may be incorporated into the ear tips of the headset. Also, the yoke 310 may incorporate an output module or interface module configured to receive an installable module 500 of a type shown in FIGS. 4-8. Alternatively, a section of the main tube or a proximate portion of the chestpiece or chestpiece handle may be configured to receive an installable module 500 of a type shown in FIGS. 4-8.

Figure 10A:
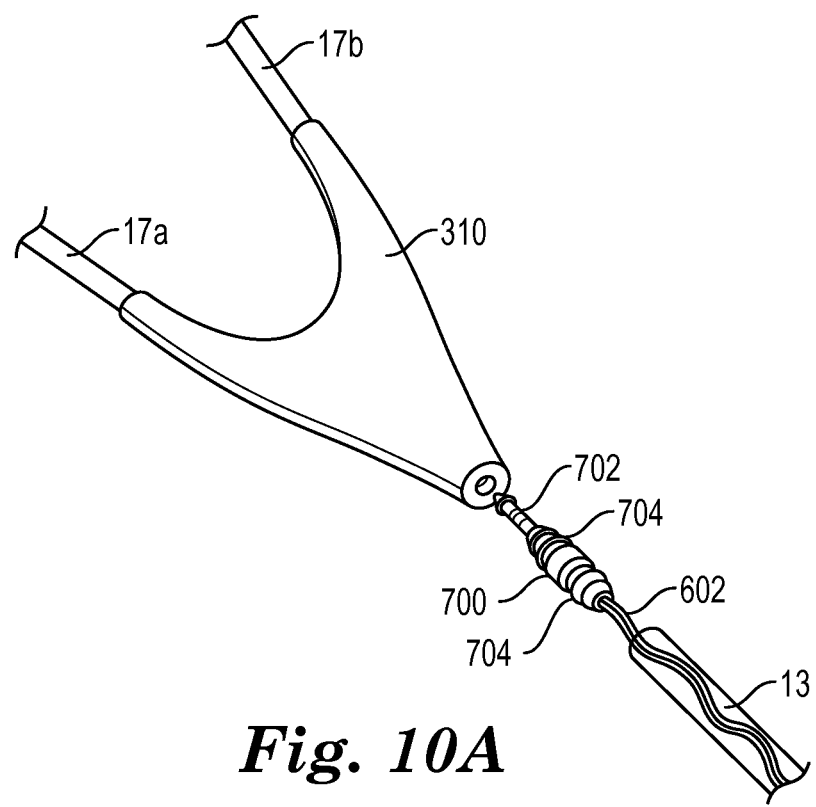
FIGS. 10A and 10B illustrate a yoke arrangement before and after assembly, respectively, the yoke arrangement including a dual barb coupler that incorporates structural and electrical connection arrangements that facilitate modular assembling of the yoke and the main tube in accordance with embodiments of the present invention.
Figure 10B:
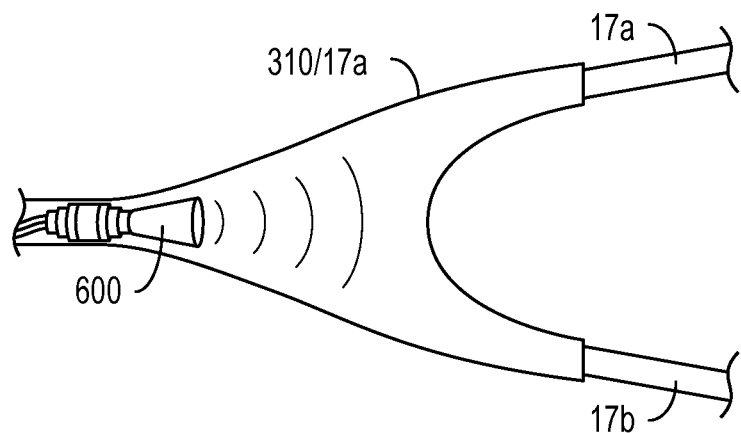

FIGS. 10A and 10B illustrate a yoke arrangement in accordance with embodiments of the present invention, before and after assembly, respectively. In this embodiment, a dual barb coupler 704 incorporates structural and electrical connection arrangements that facilitate modular assembling of the yoke 310 and main tube 13. The coupler 704 is shown to include a series of barbs that facilitate frictional pressure fitting of the coupler 704 within the lumens of the yoke 310 and main tube 13. An audio connector 702 of the coupler 704 matingly engages a receiving connector of a speaker 600 disposed in the yoke 310, as best see in FIG. 10B. Electrical conductors 602 extend from the coupler 704 to the chestpiece 110 (not shown) through the lumen of the main tube 13.

It is understood that the audio connector 702 may have a male or female configuration. It is further understood that a dual speaker arrangement, such as that shown in FIG. 9C, may be implemented in the yoke 310 shown in FIGS. 10A and 10B. In such a configuration, a splitter unit may be incorporated into the yoke 310 and configured to receive the audio connector 702. The splitter unit may have two outputs each of which is respectively coupled to one of the two speakers 600a, 600b.

Figure 11A:
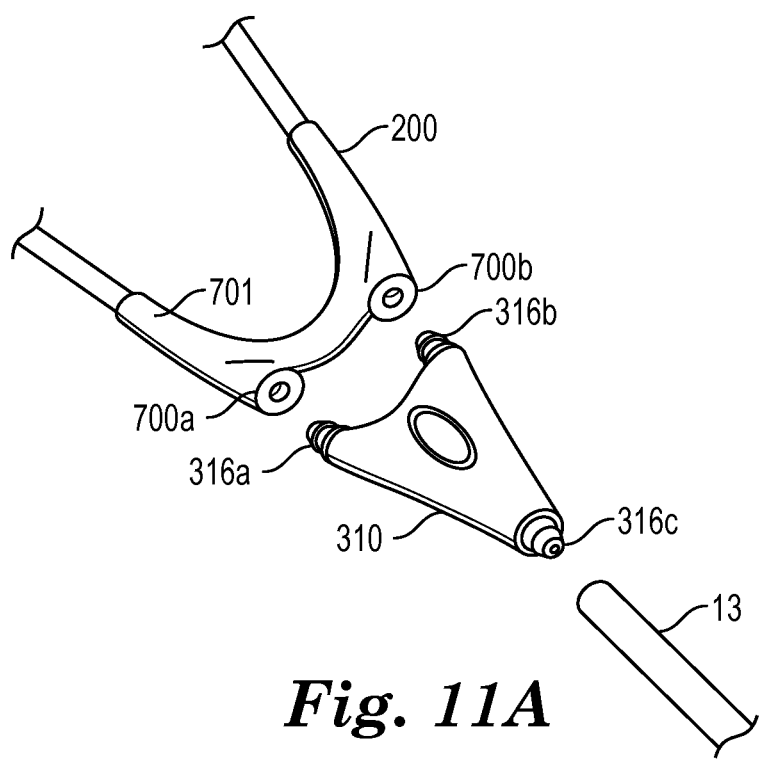
FIG. 11A shows a main tube, a yoke module that includes a main tube coupler and a pair of headset couplers, and a portion of a headset module that includes one or dual loudspeakers in accordance with embodiments of the present invention.

FIGS. 11A-11C illustrate additional configurations of a modular electronic stethoscope according to embodiments of the present invention. The modular components shown in FIGS. 11A-11C provide the user the ability to select unique tube lengths via snap fit connections between the various tubes and components.

FIG. 11A shows a main tube 13, a yoke module 310, and a portion of a headset module 200. The yoke module 310 includes a main tube coupler 316c and a pair of headset couplers 700a, 700b. The main tube coupler 316c of the yoke 310 is configured to provide mechanical and electrical coupling with the main tube 13 and chestpiece, as discussed above. The main tube coupler 316c may be the same or similar type of coupler as shown in FIG. 10A (e.g., coupler 704).

The headset couplers 700a, 700b are configured to provide mechanical and acoustic coupling with couplers 316a, and 316b, thereby allowing for transmission of sound to each of the ear tubes 17a, 17b. The u-shape portion 701 of the headset 200 shown in FIG. 11A may incorporate a conventional or custom flex band, such as the custom flex band 720 shown in FIG. 11B. A single speaker or dual speaker arrangement may be incorporated into the yoke 310. FIG. 11C illustrates an alternative speaker configuration in which dual speakers 600a, 660b are mounted in the headset 200 proximate the u-shaped portion 701 of the headset 200.

FIGS. 12A-12C illustrate an embodiment of an electronic stethoscope of the present invention that allows for convenient installation and replacement of various types of modules. The chestpiece 800 of the electronic stethoscope shown in FIG. 12A includes a recessed port 802 located at a non-obtrusive portion of the chestpiece 800. The recessed port 802 may be configured to receive a variety of different modules or a particular type of module, such as output modules. The various types of modules that may be received by recess port 802 include output modules, communications modules, processor modules, user interface modules, power supply modules, processor modules, or other electronics modules, among others. Other types of modules may be received, such as modules that allow for software upgrades or modules that include software and/processing circuitry for providing enhanced signal processing and diagnostics.

According to one implementation, module 820 shown in FIG. 12B is configured as a memory module for communication protocols (e.g., an output module). In this illustrative example, module 820 enables the stethoscope to communicate wirelessly with other external devices and systems. Module 12C enables the stethoscope to communicate with other external devices and systems via a wired connection, such as a USB connection.

Figure 13:
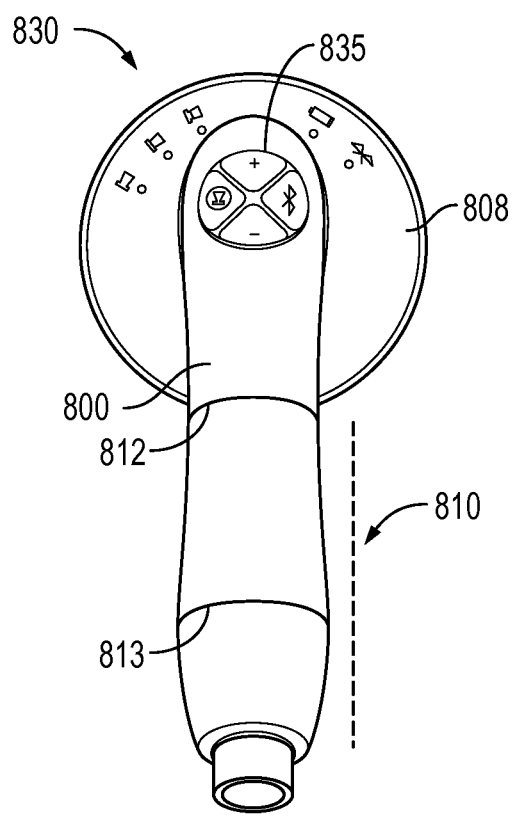
FIG. 13 illustrates an embodiment of an electronic stethoscope of the present invention that includes a user interface and detachable modules, the user interface including a number of mode and/or status indicators and mode and/or control switches.

FIG. 13 illustrates an embodiment of an electronic stethoscope of the present invention that includes a user interface. The user interface includes a number of mode and/or status indicators 830 and mode and/or control switches 835. The switches 835 may include volume or gain control switches and mode selection switches, for example. Indicators 830 may provide an indication of a selected filter mode or other information, such as battery and communication link status.

In FIG. 13, the electronic stethoscope includes a replaceable chestpiece module 808 that can be separated from the main tube portion at line 812. The attachment mechanism may include a latching mechanism and a high-density connector, for example. A handle of the chestpiece module 808 incorporates a power supply module 810 which is shown detachably coupled to the chestpiece module 808. The power supply module 810 houses one or more batteries and is configured to detachably couple with a main tube of a headset.

In one configuration, the handle of the chestpiece module 808 is detachable at line 813 proximate the main tube connection location. The handle includes a battery compartment that is easily accessed when the detachable portion of the handle 810 at line 813 is detached from the remaining handle portion of the chestpiece module 808. A loudspeaker is mounted in the detachable portion of the stethoscope handle, so that the placement of the battery within the chestpiece module 808 does not interfere with the transmission of sound to the main tube. According to this configuration, the speaker and main tube/binaural assemblies can be modularized, thereby allowing different main tube/binaural configurations to be used with a common chestpiece module 808. Mounting the loudspeaker in the detachable housing portion may also allow for better matching of speaker and main tube/binaural acoustics.

Figure 14:
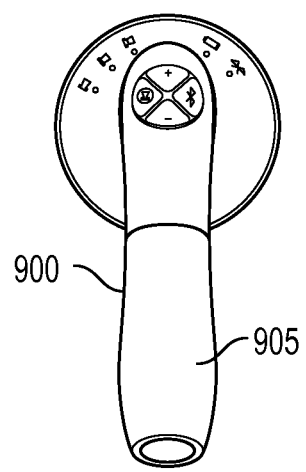
FIG. 14 illustrates a wireless electronic stethoscope that includes both a power source and a wireless communications module in accordance with embodiments of the present invention.

FIG. 14 illustrates a wireless electronic stethoscope 900. In this embodiment, the stethoscope 900 includes a module 905 that includes both a power source, such as a battery unit, and a wireless communications module, such as a Bluetooth unit. In this regard, a single module may incorporate multiple components, as is the case in other embodiments described herein. The electronic stethoscope 900 shown in FIG. 14 is configured to communicate with a wireless headset, and may also be configured to communication with an external device or system.

Figure 15:
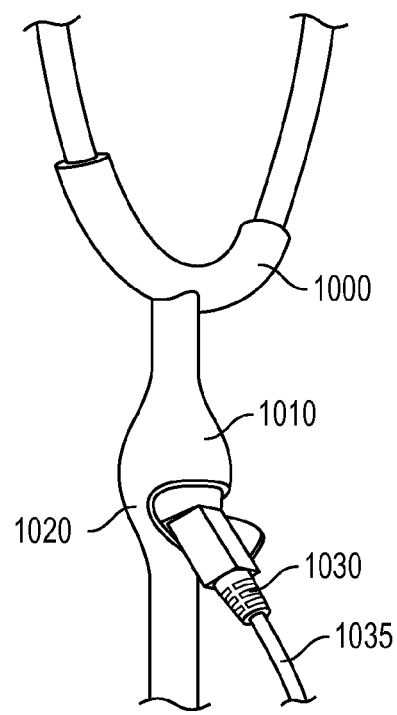
FIGS. 15 and 16 illustrate embodiments of an electronic stethoscope that allow for wired connectivity with external devices and systems in accordance with embodiments of the present invention.
Figure 16:
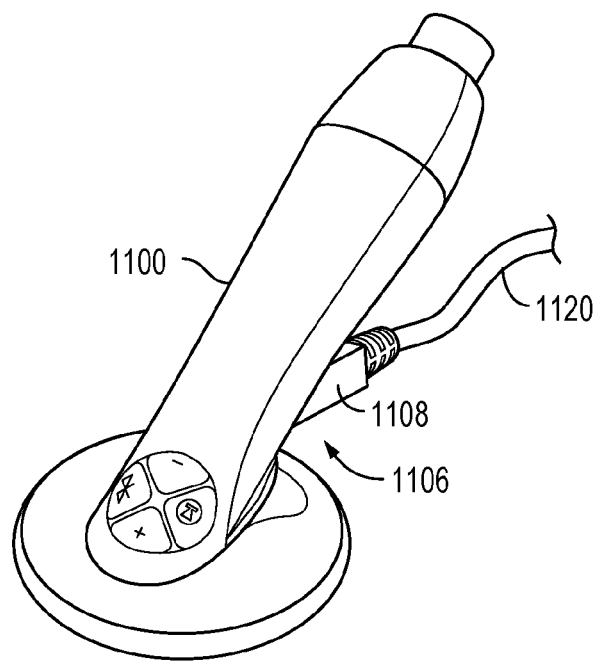

FIGS. 15 and 16 illustrate embodiments of an electronic stethoscope that allow for wired connectivity with external devices and systems. In FIG. 15, the yoke 1010 of the electronic stethoscope 1000 includes a communications interface 1020 configured to receive a wired connector 1030 of a cable 1035. The communications interface 1020 may be modularized to allow for multiple types of wired connectors 1030, such as USB and FireWire™ connectors. FIG. 16 shows the chestpiece 1108 of the electronic stethoscope 1100 that includes a communications interface 1106 configured to receive a wired connector 1108 of a cable 1120. The communications interface 1020 may be modularized to allow for multiple types of wired connectors 1030, such as USB and FireWire™ connectors.

Figure 17:
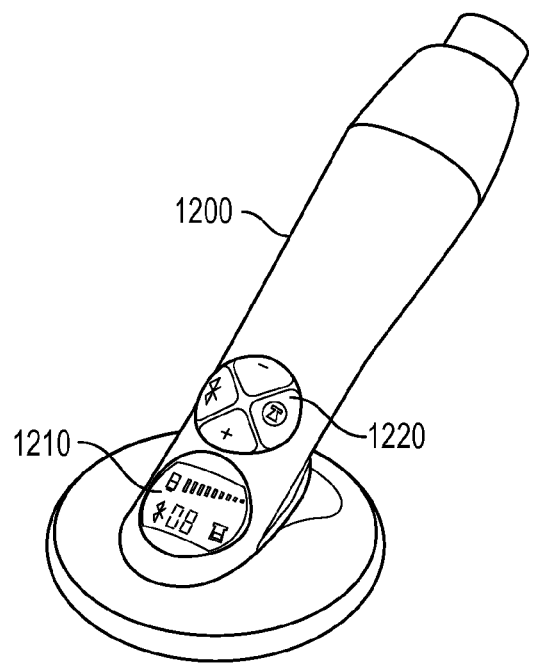
FIGS. 17 and 18 illustrate embodiments of an electronic stethoscope that include different types of user interfaces in accordance with embodiments of the present invention.
Figure 18:
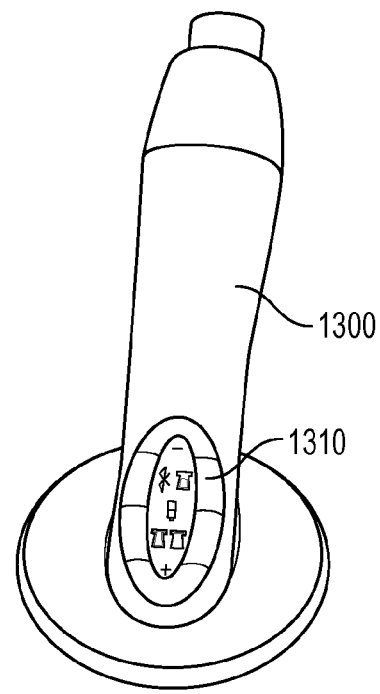

FIGS. 17 and 18 illustrate embodiments of an electronic stethoscope that include different types of user interfaces. The user interface of the electronic stethoscope 1200 shown in FIG. 17 includes an LCD display 1210 and a multiple-mode switch 1220. The LCD display 1210 may be configured to display various types of information, including mode, battery, and communication link status, as well as physiological information, such as heart rate, signal waveforms and other types of information. FIG. 18 shows an embodiment of an electronic stethoscope 1300 that includes a multiple-mode switch 1310 but excludes a display. The electronic stethoscope 1300 may optionally incorporate one or more LEDs that can provide the clinician with various types of information, as discussed previously.

Figure 19:
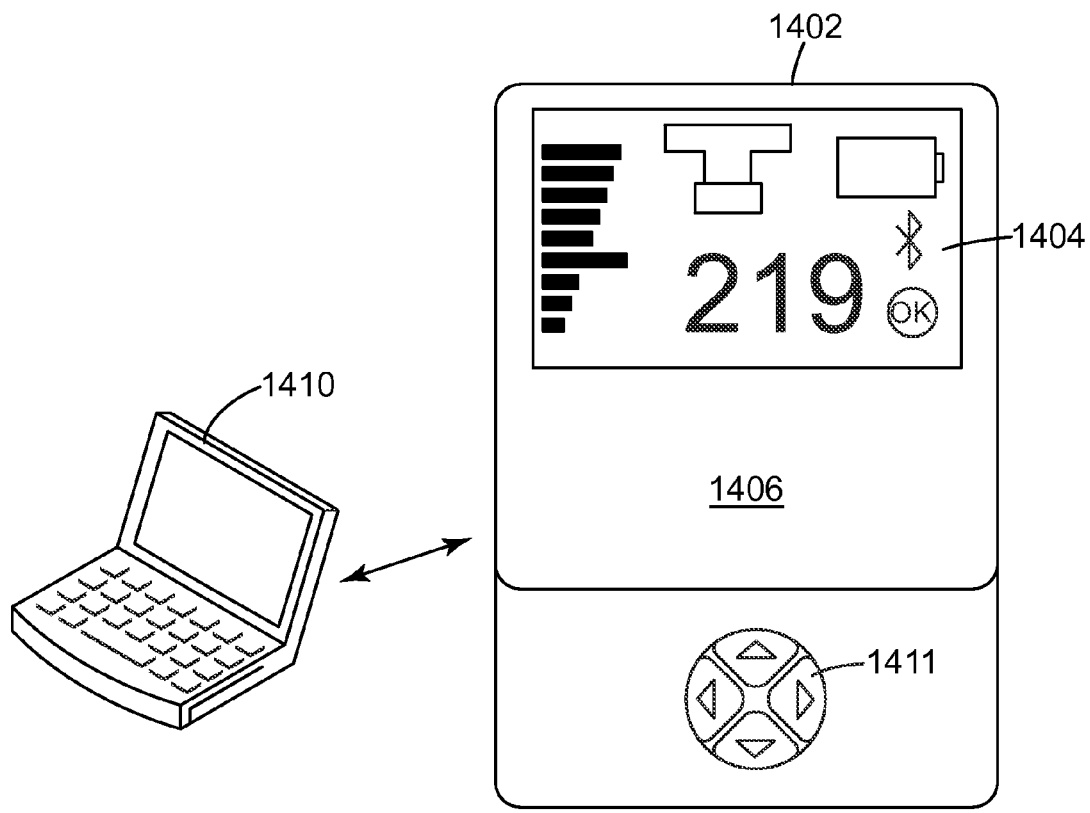
FIG. 19 shows a user interface of a biosensor, such as an electronic stethoscope, that includes a display and a multifunction control button, the display providing status and mode information about the biosensor and the patient, the display further including a display portion that can be controlled by an external device for presenting information useful to the clinician, the control button facilitating re-mapping of keys and display elements by the clinician in accordance with embodiments of the present invention.

FIG. 19 shows a user interface of a biosensor, such as an electronic stethoscope, that includes a display and a multi-function control button in accordance with embodiments of the present invention. The user interface 1402 includes a display 1404 that provides status and mode information about the biosensor and the patient. Various information may be presented in textual, numerical or graphical form or a combination thereof. Various information may be communicated aurally, such as by use of tones, beeps, or electronic voice output via a speaker.

For example, amplitude or strength of the transducer signal may be shown in bar form as is commonly used in mobile communication devices or in some other form on the display 1404. Frequency related amplitude information (e.g., power spectral density) may be shown or superimposed over the signal strength information. Battery status may be indicated graphically or in some other form, such as time remaining to depletion. The status of the biosensor's wired or wireless communication transceiver may be indicated, such as by use of a standard Bluetooth (on/off) indicator. Pairing status between the biosensor and external device 1410 may be displayed on the display 1404. The filter mode of the biosensor (e.g., bell or diaphragm mode of an electronic stethoscope) may be displayed on display 1404.

Operational status of the biosensor may be indicated by a graphical or textual indicator, such as an OK/Error indicator. Status of the patient may also be determined by the biosensor or an external system in communication with the biosensor, and this status information may be presented on the display 1404 to indicate that the patient is OK or that an anomaly has been detected. A waveform indicative of the transducer signal may be graphically presented on the display 1404.

In some embodiments, the user interface 1402 includes a display portion 1406 that can be used for a variety of purposes. For example, this portion 1406 of the display may be controlled or accessed by an external device 1410, such as a laptop or medical processing device or system, via a wired or wireless connection. Information acquired by the biosensor may be transmitted to an external device 1410 and analyzed by the device 1410 (e.g., heart murmur detection). Results of the analysis may be transmitted from the external device 1410 to the biosensor for presentation in the display portion 1406.

The biosensor or the external device 1410 may communicate to the clinician via the display portion 1406 that additional data is required or desired, and may further provide specific instructions for acquiring the additional data, such as by specifying body locations where the biosensor should be positioned to acquire the additional data. For example, the biosensor or the external device 1410 may communicate instructions to place the biosensor over a specific part of the chest so that cardiac activity data can be acquired, such as for detecting heart murmurs. After the biosensor is properly positioned and an anomaly has been detected by the biosensor or the external device 1410, the clinician may be instructed to actuate a button to initiate recording of the acquired data. After a sufficient amount of data has been acquired, the clinician may be instructed to actuate a button to terminate data recording. Alternatively, data recording may be automatically terminated when a sufficient amount of data has been acquired or when the data is no longer needed. An appropriate message is displayed to the clinician on the display portion 1406.

Attributes of the user interface 1402 of the biosensor may be redefined by cooperative operation between the display portion 1406 and the multi-mode button 1411. Redefining of user interface controls and display attributes may be implemented manually by the clinician or automatically by the biosensor, alone or in cooperation with the external device 1410. For example, attributes of the user interface may be manually or automatically redefined to enhance use of the biosensor in response to a detected anomaly or when the clinician desires to evaluate a particular portion of the patient's body or patient pathology.

The display portion 1406 and a control button 1411 (e.g., multi-mode button) of the biosensor may cooperate to facilitate re-mapping or reconfiguring of the biosensor. For example, various features and functions of the biosensor may be re-mapped or reconfigured, such as control, display, communications, sensing, detection, diagnostic, power, and other features and functions of the biosensor. Keys or buttons of the user interface 1402 may be re-mapped from one function to another. Such re-mapping may be enabled and/or limited based on a function selected by the clinician. Options for key/button re-mapping may be presented to the clinician, selection of which implements temporary re-mapping of keys, button, display elements and icons, etc. that are appropriate for the selected function.

In some configurations, the biosensor or the external device 1410 may detect an anomaly during use of the biosensor, which can automatically trigger a message on the display portion 1406 that keys, buttons, icons, and other display elements are being reconfigured or re-mapped to facilitate further investigation of the detected anomaly. The clinician may be given an option to continue with the re-mapping/reconfiguration or to return to a normal operational mode. Alternatively, re-mapping/reconfiguration may occur automatically in response to detection of an anomaly. The severity of the anomaly can be assessed by the biosensor of the external device 1410, and the manner in which re-mapping/reconfiguration occurs (e.g., automatic vs. manually by option) may be dependent on the anomaly's severity.

Figure 20:
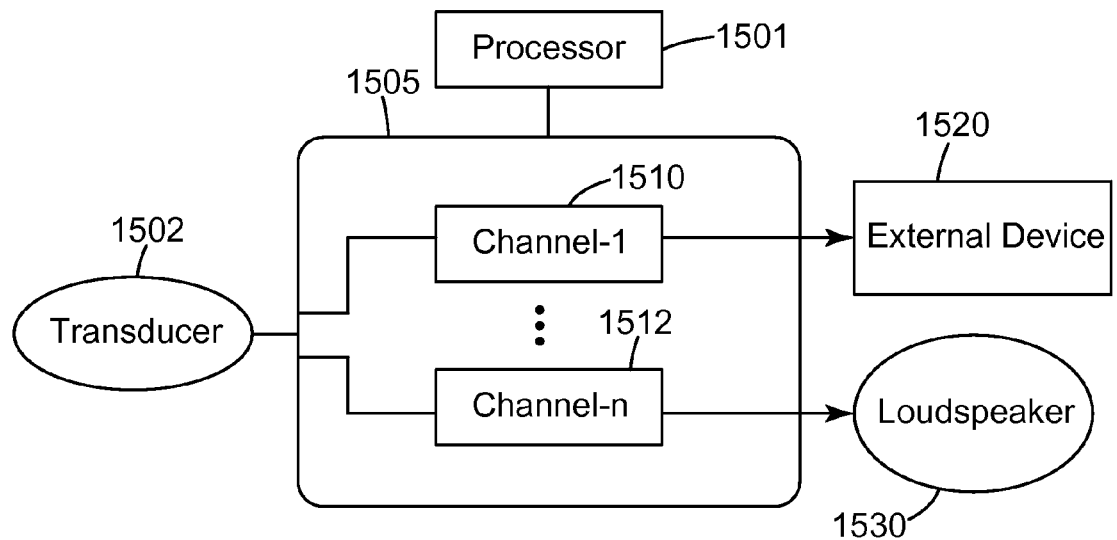
FIG. 20 is a block diagram of a signal processor that includes a multiplicity of channels each coupled to a transducer of the biosensor with each channel having different channel characteristics, the biosensor configured as a modular or a unitary biosensor in accordance with embodiments of the present invention.

Turning now to FIG. 20, there is shown a block diagram of a multiple-channel signal processor that may be incorporated in embodiments of a biosensor of the present invention. The biosensor depicted in FIG. 20 includes a transducer 1502 coupled to an input of a signal processor 1505. A main processor 1501 of the biosensor is coupled to the signal processor 1505 and may optionally be coupled to the transducer 1502. The main processor 1501 includes memory (or is coupled to memory) that stores computer/processor executable instructions for coordinating operations of the biosensor. Although shown in FIG. 20 as separate components, it is understood that the main processor 1501 and the signal processor 1505 may be integrated within a common device or chip.

The signal processor 1505 has a multiplicity of channels 1510, 1512 that are each coupled to the transducer 1502 of the biosensor. Preferably, each of the channels 1510, 1512 has, or can be configured via programming to have, different channel characteristics. In other configurations, the transducer signal information that is communicated through each of the channels 1510, 1512 can be processed in different ways for different purposes and end components.

For example, and as shown in FIG. 20, a first channel 1510 is coupled to an external device 1520 (e.g., a PC, laptop, diagnostic analyzer, other medical system) and a second channel 1512 is coupled to a loudspeaker 1530, such as a loudspeaker through which an audible form of the transducer signal is broadcast to the clinician (e.g., via a binaural arrangement, a headset, hearing aid, military helmet, or speaker of an external device). The signal processor 1501 can be configured to provide independent and programmable control of each channel 1510, 1512 relative to other channels of the signal processor 1501, and provide for processing of raw transducer signal content in different ways independently of other channels.

The first and second channel characteristics preferably differ from one another in terms of one or more characteristics. Such characteristics may include data rate, bandwidth, amplifier characteristics (wideband vs. narrowband), gain and/or gain control characteristics, level of quantization, filter characteristics, technical specification (e.g., IEEE specification), data type, and communication protocol, among others. The first channel 1510 may comprise an analog channel and the second channel 1512 may comprise a digital channel. The first and second channels 1510, 1512 may both comprise digital channels or both may comprise analog channels.

By way of further example, an analog channel of the signal processor 1505 may include channel electronics (built-in and/or programmable) that filter the raw transducer signal for purposes of enhancing the transducer signal characteristics for listening by the clinician. This filtering or other form of processing, however, may result in suppressing or removing content of the raw transducer signal that may be of value for other purposes. Although this filtered or otherwise altered form of the raw transducer signal can be communicated to an external or other device, potentially valuable information in the raw transducer signal is no longer available to such external or other device.

Employing a multi-channel signal processor 1505 as shown in FIG. 20 advantageously preserves the raw transducer signal content for independent processing via each of the separate channels 1510, 1512. For example, a first channel 1510 of the signal processor 1505 may be a channel configured to enhance listening of the raw transducer signal by a clinician, as discussed above. This channel 1510 may amplify and filter the raw transducer signal to enhance listening of specific signal content, such as low amplitude signal content (e.g., transducer signal content that is sub-audible with respect to amplitude prior to amplification).

The second channel 1512 may pass the raw transducer signal substantially unaltered (in terms of signal content) to an external device 1520. The second channel 1512 may thus have channel characteristics that minimally impact the raw transducer signal, thereby passing essentially all content of the transducer signal to an external device 1520, such as an diagnostic analyzer configured to detect anomalous or pathological conditions of the patient (e.g., heart murmurs, fluid in the lungs). Signals that pass through the first and second channels 1510, 152 may be analog or digital. For channels that include a digital channel path, the transducer signal is typically converted from analog to digital form using analog-to-digital converters. In general, negligible signal content is lost when converting the transducer signal from analog to digital form.

A biosensor that incorporates a multi-channel signal processor 1505 of the type shown in FIG. 20 may, but need not be configured to incorporate modular aspects of other embodiments. For example, a unitary biosensor that does not include a module interface of a type discussed herein may provide for enhanced usability by incorporating a multiple-channel signal processor of the present invention.

A biosensor according to the embodiments of FIGS. 19-20 and other Figures may include a processor that includes a digital signal processor and a radio in a single chip. The processor preferably allows for partial or full control of the biosensor by an external device via the radio. A suitable processor is the BlueCore5-Multimedia processor manufactured by CSR of Cambridge, United Kingdom. The BlueCore5 processor combines an on-chip Bluetooth radio, digital signal processor (DSP), stereo CODEC, a switched-mode power supply, and other components in a single chip. The BlueCore5 processor can be enabled to recognize a Bluetooth enabled external computing device (or a device via USB), for example, and allow the external device access to and control of certain functions of the biosensor, such as re-mapping of keys and displaying of information in a window of the biosensor display as discussed hereinabove.

A biosensor implemented in accordance with embodiments of the present invention may incorporate power management circuitry and methodologies, such as those disclosed in commonly owned U.S. Provisional Patent Application No. 60/919,574 filed Mar. 23, 2007 and U.S. Provisional Patent Application No. 60/919,742 filed Mar. 23, 2007 and incorporated herein by reference. For example, embodiments of an electronic biosensor of the present invention may incorporate a control system which provides advanced power and operating mode management within a highly interactive medical environment. The control system may be configured to respond to both the actions of the biosensor user as well as to communications received from other electronic devices within a medical environment.

A power management methodology of the present invention may be implemented in an electronic biosensor of a type described herein in a variety of ways. For example, activation of power-on circuitry of the biosensor can be initiated based on headset operation. Activation of power-on circuitry of the electronic biosensor can be initiated based on sensing contact between the chestpiece and the clinician's hand and/or between the chestpiece and the patient's skin or clothing. A conductive surface or pressure applied to and removed from the surface or edges of the chestpiece may be used to activate and deactivate power supply circuitry of the biosensor. A change in temperature caused by handling the biosensor (e.g., clinician touching and/or patient contact with the chestpiece) may be sensed and used to activate and deactivate power supply circuitry of the biosensor. Powering on and off the biosensor may be controlled via measuring changes in impedance, capacitance, resistance or other electrical parameter, such as when the biosensor ear tips are placed into and removed from ear canals. Powering on and off the biosensor may be controlled by a mechanical, electrical, magnetic or optical switch or sensor, or a combination of such switches and sensors.

Other sensor configurations are contemplated that can be implemented in or are associated with the chestpiece of the electronic biosensor rather than the headset. It is understood that a combination of sensors in the chestpiece and the headset may be used to sense and/or verify imminent need for biosensor usage by the clinician. Examples of such sensors include sensors that detect the relative displacement or rotation of a diaphragm or other sensor assembly with respect to the main structure of the chestpiece. Other useful sensors include sensors that detect the flexion, bending, rotation, or torsion of the stem of the chestpiece relative to the main structure of the chestpiece. Sensors that sense deformation of a structure on the chestpiece, such as areas used by the clinician when gripping the biosensor, may also be employed. Resistance sensor affected by external conductance such as that presented by the skin of the user when gripping the chestpiece may be employed.

Various other approaches for sensing imminent clinician need for biosensor usage may be employed, such as sensors that sense a differential change of a parameter associated with human contact or release of contact. Such sensors may be configured to sense a differential change at the wall of the chestpiece due to the presence of a hand gripping the chestpiece. Such differential changes may be temperature, light, current, or voltage change. In one such implementation, a change in chestpiece temperature due to heating by a user's hand may be sensed and compared to a threshold, such as an ambient or other baseline temperature. In such an implementation, a relatively inaccessible surface of chestpiece may be used as a reference temperature location.

In some embodiments, power management approach of the present invention may provide for activation of power circuitry and other circuitry of a patient-external device that communicates with the electronic biosensor, such as a PDA, PC or other patient-external device. For example, initiation of the electronic biosensor's automatic power-on procedure may include generation of a command that causes the patient-external device to power-up, such as from a sleep mode. The command generated by the electronic biosensor may also initiate a software routine in the patient-external device that configures the external device to operate cooperatively with the electronic biosensor, such as by launching application software designed to facilitate communication and/or interaction with the electronic biosensor.

Embodiments of the present invention are directed to methods of assembling an electronic medical device, such as a biosensor or an electronic stethoscope of a type discussed hereinabove. According to one approach, a computer based system, such as a web based automated system, is configured to facilitate selection of medical devices, modules, and other options according to the needs of an end-customer, such as a clinician. The computer based system preferably uses known user input devices, applications, and interfaces to facilitate on-line transactions by a remote end-user (e.g., purchaser). A menu of medical devices and modules may be presented from which a particular medical device may be selected.

Based on the selected medical device, such as a stethoscope, a menu of models and modules may be presented. The end-user may select a desired model and any desired modules. The stethoscope may thus be custom ordered and subsequently assembled based on the model, modules, and other information selected by, or input from, the end-user. After finalizing the order, which may include payment by credit card for example, a build order is generated, from which the specified stethoscope is assembled at a manufacturing or assembly location. The stethoscope(s) may be shipped directly to the purchaser via standard mail or shipping services, for example.

An automated assembly methodology of the present invention provides for the selection of desired stethoscope components (functional requirement) as well as selection of stethoscope components that will comfortably fit the end-user. For example, the end-user preferably selects ear tube and main tube lengths that best accommodate the size and shape of the end-user. Ear tips may likewise be selected by the end-user to enhance comfort, wearability or functionality, such as in the case of users that have a hearing aid. The size and shape of the chestpiece may be based on the hand size of the end-user (e.g., clinician) or the type of the patient (adults versus children or infants).

A modular approach to configuring and assembling electronic stethoscopes or other electronic medical devices in accordance with the present invention provides the opportunity to support a "personal stethoscope" business model, in which end customers may configure a stethoscope according to their needs using standardized modules via an automated computerized system, such as a web-based commerce system. A modular approach to configuring and assembling electronic stethoscopes or other electronic medical devices in accordance with the present invention also provides the opportunity to create and maintain a database that contains current and historical configuration data for any number of medical devices. Changes to the configuration of a particular medical device (e.g., a processor module change of a stethoscope) may be captured automatically, and such change data may be used to update a medical device configuration database. Automated updating may be accomplished based on the ordering system discussed above or from the medical device itself, which may upload its current configuration data (e.g., identification information, version information (hardware and/or software configuration details), and operating status information for all modules currently installed in the medical device) to the medical device configuration database, typically via a network connection.

In the description of the various embodiments provided above, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention. It is further understood that systems, devices or methods according to the present invention may include one or more of the features, structures, methods, or combinations thereof described herein. For example, a device or system may be implemented to include one or more of the advantageous features and/or processes described above. In particular, features and/or processes shown in FIGS. 3, 4A, 4B, 5A, 5B, 6, 7, 8A, 8B, 18, and 20 may be implemented in the biosensor embodiments shown in FIGS. 1, 9A-9C, 10A, 10B, 11A-11C, 12A-12C, and 13-18 or in systems that incorporate such biosensor embodiments. Moreover, selected features shown in FIGS. 1-20 may be combined in various manners beyond those specifically described herein to define useful embodiments of the present invention. It is intended that such devices, systems or processes, however, need not include all of the features described herein, but may be implemented to include selected features that provide for useful structures and/or functionality.

The foregoing description of the various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A modular electronic biosensor, comprising:
    a housing configured for hand-held manipulation relative to a person's body surface and comprising a base module, the housing comprising a plurality of module interfaces configured to engage a plurality of detachable modules, the plurality of detachable modules comprising at least one of a detachable transducer module and a detachable output module, the transducer module comprising a transducer configured to sense a property of the person's body and the output module configured to output a signal that includes transducer signal information, each of the plurality of module interfaces comprising:
        a module connector configured to be coupled to a connector of a detachable module of the plurality of detachable modules and to facilitate signal transmission between the respective connectors;
        a mechanical retention mechanism configured to detachably and retentively engage a mechanical engagement arrangement of the detachable module; and
        a sealing arrangement disposed to provide sealing between the base module and the detachable module when the detachable module is attached to the base module;
    a processor coupled to each of the module connectors and configured to communicatively couple with each of the detachable modules when the detachable modules are attached to the base module; and
    the housing preserving ergonomic efficiency for facilitating hand-held manipulation relative to the person's body surface after attachment of the detachable modules to the base module.

2. The biosensor of claim 1, wherein a first module interface of the plurality of module interfaces is configured to engage the detachable transducer module and a second module interface of the plurality of module interfaces is configured to engage the detachable output module.

3. The biosensor of claim 1, wherein a first module interface of the plurality of module interfaces is configured to engage the detachable transducer module.

4. The biosensor of claim 1, wherein the base module comprises a transducer configured to sense a property of the person's body, and a first module interface of the plurality of module interfaces is configured to engage the detachable output module, the processor communicatively coupled to the transducer of the base module.

5. The biosensor of claim 1, wherein the base module comprises a radio, and a first module interface of the plurality of module interfaces is configured to engage the detachable output module, the detachable output module comprising memory for storing software that configures the radio of the base module, the software or the processor capable of changing the modality of communication after attachment of the detachable output module.

6. The biosensor of claim 1, wherein a first module interface of the plurality of module interfaces is configured to engage the detachable output module, the detachable output module comprising a radio one of the detachable output module and base module comprising memory for storing software that configures the radio, the software or the processor capable of changing the modality of communication after attachment of the detachable output module.

7. The biosensor of claim 1, wherein a first module interface of the plurality of module interfaces is configured to engage the detachable output module, at least one of the detachable output module and the base module comprising a power interface configured to facilitate connection between the biosensor and an external power source.

8. The biosensor of claim 1, comprising a primary power source and a secondary power source, the primary power source disposed in the base module and the secondary power source disposed in at least one of the detachable transducer module and the detachable output module.

9. A modular electronic biosensor, comprising:
    a housing configured for hand-held manipulation relative to a person's body surface and comprising a base module, the housing comprising a module interface configured to engage one of a plurality of detachable and interchangeable modules, the plurality of detachable and interchangeable modules comprising at least one of a detachable transducer module and a detachable output module, the transducer module comprising a transducer configured to sense a property of the person's body and the output module configured to output a signal that includes transducer signal information, the module interface comprising:
        a module connector configured to be coupled to a connector of the detachable module and to facilitate signal transmission between the respective connectors;
        a mechanical retention mechanism configured to detachably and retentively engage a mechanical engagement arrangement of the detachable module; and a sealing arrangement disposed to provide sealing between the base module and the detachable module when the detachable module is attached to the base module;

a processor coupled to the module connector and configured to communicatively couple with each of the detachable and interchangeable modules when attached to the base module; and the housing preserving ergonomic efficiency for facilitating hand-held manipulation relative to the person's body surface after attachment of the detachable module to the base module.

10. The biosensor of claim 9, wherein the processor is disposed in the base module.

11. The biosensor of claim 9, wherein the processor is disposed in at least one of the plurality of detachable modules.

12. The biosensor of claim 9, wherein the processor is distributed between the base module and each of the plurality of detachable modules.

13. The biosensor of claim 9, wherein the transducer is configured to sense a manifestation of acoustic energy produced by matter of biological origin.

14. The biosensor of claim 9, wherein the transducer is configured to sense at least one of:
flow or volume of a fluid,
a biopotential, and
a structural or compositional property of the person's body.

15. The biosensor of claim 9, wherein the transducer comprises an ultrasound sensor or a Doppler ultrasonic sensor.

16. The biosensor of claim 9, wherein the base module comprises a transducer configured to sense a property of the person's body, and the module interface is configured to engage the detachable output module, the processor communicatively coupled to the transducer of the base module.

17. A system comprising:
the biosensor of claim 9,
a wired headset, and
an interface for coupling the headset to the biosensor.

18. A system comprising:
the biosensor of claim 9,
a wireless headset, and
an interface for coupling the headset to the biosensor.

19. A system comprising:
the biosensor of claim 9,
a military helmet incorporating an integral wireless headset, and
an interface for coupling the wireless headset to the biosensor.

20. A system comprising:
The biosensor of claim 9,
a hearing aid and
an interface for coupling the hearing aid to the biosensor.

21. The biosensor of claim 9, comprising a user interface including a display provided on at least one of:
the base module, and
at least one of the plurality of detachable modules.

22. The biosensor of claim 9, wherein the base module comprises a radio, and the module interface is configured to engage the detachable output module, the detachable output module comprising memory for storing software that configures the radio of the base module, the software or the processor capable of changing the modality of communication after attachment of the detachable output module.

23. The biosensor of claim 9, wherein the module interface is configured to engage the detachable output module, the detachable output module comprising a radio, one of the detachable output module and base module comprising memory for storing software that configures the radio, the software or the processor capable of changing the modality of communication after attachment of the detachable output module.

24. The biosensor of claim 9, wherein the module interface is configured to engage the detachable output module, at least one of the detachable output module and the base module comprising a power interface configured to facilitate connection between the biosensor and an external power source.

25. The biosensor of claim 9, wherein the processor comprises a signal processor having an input that receives the transducer signal information and at least a first channel and a second channel each coupled to the input, the first channel coupled to a loudspeaker and having first channel characteristics, the second channel coupled to an external device and having second channel characteristics different from the first channel characteristics.

26. The biosensor of claim 1, wherein the housing comprises a first housing, wherein at least one of the detachable modules comprises a module housing, wherein the module housing corresponds to the profile of the first housing.

27. The biosensor of claim 9, wherein the housing comprises a first housing, wherein at least one of the detachable modules comprises a module housing, wherein the first housing comprises a recessed port including the module interface and adapted to receive the module housing.

28. The biosensor of claim 9, wherein the sealing arrangement provides a splash-proof level of sealing.

* * * * *